(12) United States Patent
Crudden

(10) Patent No.: US 8,895,044 B2
(45) Date of Patent: Nov. 25, 2014

(54) FOOD PRESERVATION COMPOSITIONS AND METHODS

(75) Inventor: Joseph J. Crudden, Hudson, NH (US)

(73) Assignee: Sciessent, LLC, Wakefield, MA (US)

( * ) Notice: Subject to any disclaimer, the term of this patent is extended or adjusted under 35 U.S.C. 154(b) by 1024 days.

(21) Appl. No.: 12/154,131

(22) Filed: May 19, 2008

(65) Prior Publication Data

US 2008/0292722 A1 Nov. 27, 2008

Related U.S. Application Data

(60) Provisional application No. 60/930,913, filed on May 18, 2007.

(51) Int. Cl.
| | |
|---|---|
| A01N 25/02 | (2006.01) |
| A01N 25/04 | (2006.01) |
| A01N 25/12 | (2006.01) |
| A01N 59/16 | (2006.01) |
| A01N 59/20 | (2006.01) |
| A23L 3/3463 | (2006.01) |
| A23L 3/3508 | (2006.01) |
| A23L 3/3526 | (2006.01) |
| A23L 3/3535 | (2006.01) |
| A23L 3/358 | (2006.01) |

(52) U.S. Cl.
CPC ............... *A01N 25/04* (2013.01); *A01N 25/12* (2013.01); *A01N 59/16* (2013.01); *A01N 59/20* (2013.01); *A23L 3/3463* (2013.01); *A23L 3/3508* (2013.01); *A23L 3/3526* (2013.01); *A23L 3/3535* (2013.01); *A23L 3/358* (2013.01)
USPC ...................................................... 424/417

(58) Field of Classification Search
None
See application file for complete search history.

(56) References Cited

U.S. PATENT DOCUMENTS

| | | | |
|---|---|---|---|
| 2,655,460 A | 12/1949 | Kise | |
| 3,404,987 A | 10/1968 | Kooistra | |
| 4,055,655 A | 10/1977 | Maurer et al. | |
| 4,332,791 A | 6/1982 | Reaf et al. | |
| 4,743,454 A | 5/1988 | Tomes | |
| 4,915,955 A | 4/1990 | Gomori | |
| 5,174,990 A | 12/1992 | Douglas | |
| 5,635,279 A * | 6/1997 | Ma et al. ....................... | 428/174 |
| 5,753,290 A * | 5/1998 | Adam ........................... | 426/412 |
| 5,804,591 A * | 9/1998 | Valcke et al. ................. | 514/383 |
| 5,968,539 A * | 10/1999 | Beerse et al. ................. | 424/405 |
| 6,294,186 B1 | 9/2001 | Beerse et al. | |
| 6,303,039 B1 | 10/2001 | Back et al. | |
| 6,572,908 B2 | 6/2003 | Kemp et al. | |
| 6,638,431 B2 | 10/2003 | Back et al. | |
| 6,773,737 B1 * | 8/2004 | Roselle et al. ............... | 426/335 |
| 6,797,302 B1 * | 9/2004 | Ben Yehuda et al. ......... | 426/335 |
| 7,060,302 B1 | 6/2006 | Hickok | |
| 7,147,872 B2 | 12/2006 | Ben-Yehuda et al. | |
| 7,163,709 B2 | 1/2007 | Cook et al. | |
| 7,192,618 B2 | 3/2007 | Cummins et al. | |
| 7,435,359 B2 * | 10/2008 | Scholer ....................... | 252/389.23 |
| 7,658,959 B2 * | 2/2010 | Koefod et al. ............... | 426/335 |
| 2002/0025344 A1 * | 2/2002 | Newman et al. .............. | 424/618 |
| 2003/0198689 A1 | 10/2003 | Arata | |
| 2004/0137076 A1 | 7/2004 | Yamauchi et al. | |
| 2004/0167220 A1 | 8/2004 | Horst et al. | |
| 2005/0079227 A1 * | 4/2005 | Tate .............................. | 424/634 |
| 2005/0191365 A1 | 9/2005 | Creasey et al. | |
| 2005/0191395 A1 | 9/2005 | Creasey et al. | |
| 2005/0202066 A1 * | 9/2005 | Arata ............................ | 424/443 |
| 2006/0024412 A1 * | 2/2006 | Cha et al. ...................... | 426/326 |
| 2006/0030506 A1 | 2/2006 | Song et al. | |
| 2006/0099152 A1 * | 5/2006 | Day et al. ..................... | 424/49 |
| 2006/0122082 A1 | 6/2006 | Paul | |
| 2006/0189483 A1 | 8/2006 | Hickok | |
| 2007/0128295 A1 | 6/2007 | Kennedy | |
| 2007/0232693 A1 * | 10/2007 | Abou-Nemeh ............... | 514/492 |
| 2007/0248673 A1 * | 10/2007 | Martinez et al. ............. | 424/486 |
| 2007/0269563 A1 * | 11/2007 | Mixon et al. ................. | 426/332 |
| 2009/0305888 A1 * | 12/2009 | Li et al. ........................ | 504/101 |

FOREIGN PATENT DOCUMENTS

| | | |
|---|---|---|
| EP | 0150959 A2 | 8/1985 |
| JP | 55027164 | 2/1980 |
| JP | 59055177 | 3/1984 |
| JP | 2004175686 | 6/2004 |
| KR | 20060034258 | 3/2006 |
| WO | 9800012 | 1/1998 |
| WO | WO 9937172 * | 7/1999 |
| WO | 0027390 | 5/2000 |
| WO | 0296202 A1 | 5/2002 |
| WO | 03028455 A1 | 4/2003 |
| WO | 03039766 A1 | 5/2003 |
| WO | 03053170 A1 | 7/2003 |
| WO | 2005023022 A1 | 3/2005 |
| WO | 2006062845 A2 | 6/2006 |
| WO | WO 2006002671 * | 12/2006 |
| WO | 2007147267 A1 | 12/2007 |

OTHER PUBLICATIONS

Hanashita et al JP2004204101 7/22/04HCAPLLUS abstract 2004:125415, doc. # 141:125415 liquid detergents mild to skin for kitchen.*

* cited by examiner

*Primary Examiner* — Anand Desai
*Assistant Examiner* — Melissa Mercier
(74) *Attorney, Agent, or Firm* — Edward K Welch, II; IP&L Solutions

(57) ABSTRACT

A method of protecting food or delaying the onset of food spoilage said method comprising applying a protective bioactive composition to the food or the packing or packaging in which the food is stored.

22 Claims, No Drawings

FOOD PRESERVATION COMPOSITIONS AND METHODS

The present patent application claims the benefit of prior filed U.S. Provisional Patent Application No. 60/930,913, filed May 18, 2007 and entitled "Bioactive Compositions and Use Thereof" which is hereby incorporated herein in its entirety by reference.

FIELD OF THE INVENTION

The present invention relates to novel bioactive compositions for the preservation of fresh foods and feeds, especially fruits, nuts, vegetables, grains, and the like. In particular there are provided novel antimicrobial metal ion-acidic solutions having low levels of bioactive metal ion, alone or, preferably, in further combination with one or more surfactants capable of interacting with cell wall membranes of microorganisms, especially pathogenic microbes. These bioactive compositions are found to be especially suitable in killing and/or controlling or inhibiting the growth and proliferation of microorganisms, especially fungi and/or bacteria, responsible for the quick decay and spoilage of fresh foods.

BACKGROUND OF THE INVENTION

Bioactive materials for killing or inhibiting the growth and/or proliferation/spreading of bacteria, fungi, and other microorganisms have long been sought and employed in society. Their use dates back centuries, if not thousands of years. Early applications had ranged from pharmaceutical or health related applications to disinfectant and purification applications and more. More recent applications include a whole host of uses, with the largest use, by volume, seen in the agricultural industry. Perhaps one of the earliest bioactive materials was metallic silver and, subsequently, silver salts.

While early bioactive agents were most often metals and simple metal salts, modern science and chemical synthesis has enabled the development and production of synthetic agents, most often organic and organometallic agents, for antibacterial, antifungal and other like applications. Indeed, for many applications, especially pharmaceutical applications, the organic agents have, for the most part, eclipsed the use of inorganic bioactive agents. While inorganic and organometallic materials still command a significant market share of the agrichemical business, their use is limited due to their health and safety concerns, especially from an environment perspective.

Despite the great success and huge market share/volume commanded by organic pharmaceutical, antibacterial and agrochemical agents, they have not come without cost and consequences. In all areas of applications, a marked and growing trend has emerged: namely the manifestation and spreading of a resistance to such organic agents in most all, if not all, microorganisms. While this resistance is neither universal nor complete, it is growing and involves more and more organic agents. Furthermore, as their resistance grows, so too does their apparent virulence as well as their ability to quickly adapt to and manifest resistance to new bioactive agents and combinations thereof. In this respect, we are all well aware of the growing resistance of bacteria, especially pathogenic bacteria, to traditional pharmaceutical agents and the subsequent appearance of what are commonly referred to as superbugs: pathogenic bacteria that show strong resistance to traditional organic antibacterial and pharmaceutical agents. The same trend has been seen in the agrichemical industry where, for example, despite the great fanfare and promise behind the introduction of strobilurin fungicides in the mid-1990s, resistance had been found after just a couple years use in certain applications.

And, whether a direct or indirect consequence of the appearance of superbugs and/or the growing awareness of the ease by which bacteria can spread combined with an increasing concern for potentially pandemic diseases such as SARS and Bird Flu, we have become a population that is more and more pre-occupied with hygiene and general cleanliness. Consequently, there has been a huge proliferation and exponential growth in the widespread and indiscriminate use and application of cleansers and disinfectants that contain organic antimicrobial agents as well as in the production, marketing and use of a whole host of consumer products having one or more antimicrobial agents incorporated therein, all in an effort to ward off exposure to bacteria and, especially, superbugs. However, this indiscriminate use of organic agents has come with, or at least presents the possibility for, an overall increase in antimicrobial resistant organisms. By eradicating the weaker organisms, the stronger and, most often more damaging, organisms are left.

Such concerns, however, are not limited to our living environment, but also arise with respect to our food supply as well. Specifically, while resistance is certainly of great concern, perhaps and even greater concern is the human and environmental toll associated with the widespread use of antimicrobial agents: not just organic but inorganic, especially metals, as well. For more than half a century now, more and more scientific literature has appeared correlating long-term exposure to (direct and indirect) and use of organic agrichemicals to various diseases and teratogenic, mutanogenic, and other adverse health consequences in animals and, more importantly, the human population. Perhaps the watershed of this awareness is represented by the outcry relating to the use of DDT and like pesticide agents in the 1960s. However, such concerns are not limited to the organic pesticides: indeed, heavy metals, while extremely effective as or as a component of agrichemical agents, present equally troublesome issues.

Generally speaking, agrichemicals have long been under close scrutiny owing to known and increasing correlation between their use and/or exposure and the appearance of birth defects, cancer, and other diseases, not just in humans, but in plants and animals generally. Exposure routes are plenty with one of the chief exposure routes being water supplies that have or may become contaminated with such agrichemicals due to their and/or their by-product's solubility and long half-lives. Another exposure source concern is inhalation from dust blown up from the fields, from wayward aerosols and/or particulates during aerial spraying and dusting, respectively, and from exposure to the clothing of workers who, themselves, were exposed in the fields or during application.

While the foregoing present significant exposure concerns, perhaps the greatest exposure route, simply because it affects all people wherever they are located, is the food chain. For decades now, we've been challenged to limit the consumption of certain fish due to heavy metal, especially mercury, bioaccumulation. Similarly, we've seen one agrichemical after another pulled from use or more severely restricted in its use owing to the appearance of certain human health concerns and a concomitant public outcry. For example, in the late 1980's, the use of Alar, a very widely used and very beneficial agrichemical, on apples was "voluntarily" discontinued due to increasing health concerns pertaining to residual amounts of the agrichemical and/or its by-products in the apples and in apple juice produced from the treated apples. Consequently, crop yields and, more importantly, the esthetic look and shelf-life of the apple crops fell. Similar consequences have befallen more and more agrichemicals, putting more stress on the remaining agrichemicals to carry the weight, especially as mankind looks to generate more and more crop from a given land area.

While there is a growing trend and push to grow organically and eliminate agrichemicals, such options are not practical and, more importantly, result in crops that have a shorter shelf life and, in many instances, do not look as fresh and appetizing as those that have benefited from agrichemicals, either during the growing process or as a pre-harvest/post-harvest treatment. Additionally, with the agricultural economy now a world-wide economy with fruits and vegetables being flown all over the world to enable year-round enjoyment of seasonal products, there is a growing need to improve shell life and ward off spoilage. Furthermore, and perhaps more importantly, there is an ever growing concern with the safety of our foods and foodstuffs: particularly from a food borne illness perspective. In particular, several significant incidents in the United States involving pathogenic bacteria contaminated spinach and green leaf products led to several deaths and serious illnesses as well as the loss of hundreds of millions of dollars in crop destruction and product recalls. Such concerns are not just with respect to agriculturally grown foods and foodstuffs, but apply to protein based food and feed products, including fish, poultry, eggs, meats, and the like, as well.

In light of the foregoing, it is clear that the agricultural industry, indeed the food supply chain, is in a huge quandary, use pre-harvest and post-harvest agrichemicals to preserve and protect food products from spoilage and bacterial contamination or protect the environment and food chain from agrichemical build-up and contamination and microorganism resistance. With other food products, especially protein products, again there is the desire for long shelf-life and reduced spoilage and bacterial contamination while avoiding or at least minimizing any environmental and/or food contamination with preservative or other agrichemical agents.

Thus, there is a need for pre-harvest treatments for food crops that minimize any release or exposure of harmful agrichemical actives or agents, especially any that may tend to bio-accumulate, into the environment and/or to those applying the same.

Similarly, there is a need for post-harvest treatments for food crops that have minimal risk of human health exposure and/or exposure related concerns.

Similarly, there is a continuing need for food preservative agents that can be employed for inhibiting spoilage, especially that arising from microorganisms, of foods and food stuffs, as well as feed crops.

In particular, there is a need for inorganic antimicrobial, antifungal, antibacterial, etc., agents that may be used universally, or nearly so, on food crops and products without concern, or certainly with reduced concern, for environmental contamination and toxicity.

Similarly, there is a need for inorganic agents that are stable and easy to use, and provide good short term and, preferably, longer term efficacy as compared to many of the current short lived organic agents.

SUMMARY OF THE INVENTION

In accordance with the present invention there are provided protective bioactive compositions useful in the pre-harvest and post-harvest treatment of foodstuffs to inhibit cellular growth of known pathogenic, indicator and spoilage bacteria and molds, said products comprising an acid solution having a pH of less than 6 whose acid concentration is from about 0.01% to about 10%; at least one antimicrobial metal ion source partially, or preferably, fully dissolved therein, and, optionally, though preferably, at least one surfactant wherein the acid is present in a molar excess relative to the antimicrobial metal ions and the level of the antimicrobial metal ion in the solution is from about 1 ppm to about 500 ppm, preferably from about 1 to about 300 ppm, more preferably about 2 ppm to about 100 ppm, most preferably from about 5 to about 50 ppm, in the case of a single antimicrobial metal ion and from about 2 ppm to about 1000 ppm, preferably from about 2 ppm to about 500 ppm, more preferably from about 5 ppm to 300 ppm, most preferably from about 5 ppm to about 150 ppm in the case of multiple metal ions. Preferably these compositions will have at least a 2× molar excess, preferably at least a 5× molar excess of the acid relative to the metal ion(s), and a pH of from about 1.5 to about 5, most preferably from about 2 to about 4. Where the acid is other than a mineral acid, the product should have at least one anionic, non-ionic and/or amphoteric surfactant that impacts or interacts with cell wall membranes of microorganisms, especially pathogenic microbes, or the function thereof.

The protective bioactive compositions of the present invention may further include binder systems, thickeners, wetting agents, and/or other surfactants that are approved for human consumption to better apply and hold the products to the foodstuffs to which they are applied. Application may be by way of, for example, spraying or dusting in the case of pre-harvest application or spraying, dipping, coating, etc. in the case of post-harvest application. Besides direct application to the foodstuffs, these compositions may also be applied to the packing and/or packaging into which the foodstuffs are placed for storage, transport and/or distribution or sale. For example, cellulosic and other liquid absorbent packing materials and packaging may be treated or saturated with the protective compositions. Similarly, the protective bioactive compositions may be frozen or incorporated into ice that is use as a packing material for the foodstuffs.

According to another embodiment of the present invention, there are provided packing and packaging materials for food products which packing or packaging materials are treated with or made using the aforementioned protective bioactive compositions. Specifically, cellulosics and other absorbent and/or adsorbent packing materials are treated or saturated with the protective bioactive compositions to inhibit the spoilage and extend the shelf life of food stuffs stored and/or shipped in said packing or packaging. In addition, and alternatively, the packing may be ice, at least a portion of which is made from the protective bioactive composition.

According to yet another embodiment of the present invention, there is provided a method of protecting foodstuffs from cellular growth of known pathogenic, indicator and spoilage bacteria and/or molds, said method comprising applying to said foodstuffs either at the pre-harvest or post-harvest stage, a protective bioactive composition comprising an acid solution having a pH of less than 6 whose acid concentration is from about 0.01% to about 10%; at least one antimicrobial metal ion source partially, or preferably, fully dissolved therein, and, optionally, though preferably, at least one surfactant wherein the acid is present in a molar excess relative to the antimicrobial metal ions and the level of the antimicrobial metal ion in the solution is from about 1 ppm to about 500 ppm, preferably from about 1 to about 300 ppm, more preferably about 2 ppm to about 100 ppm, most preferably from about 5 to about 50 ppm, in the case of a single antimicrobial metal ion and from about 2 ppm to about 1000 ppm, preferably from about 2 ppm to about 500 ppm, more preferably from about 5 ppm to 300 ppm, most preferably from about 5 ppm to about 150 ppm in the case of multiple metal ions. Preferably these compositions will have at least a 2× molar excess, preferably at least a 5× molar excess of the acid relative to the metal ion(s), and a pH of from about 1.5 to about 5, most preferably from about 2 to about 4. Where the acid is other than a mineral acid, the product should have at least one anionic, non-ionic and/or amphoteric surfactant that impacts or interacts with cell wall membranes of microorganisms, especially pathogenic microbes, or the function thereof. These products may further include binder systems and/or other surfactants that are approved for human consumption to better apply and hold the protective composition for the foodstuffs.

Finally, according to yet another embodiment of the present invention, there is provided a method of protecting foodstuffs from cellular growth of known pathogenic, indicator and spoilage bacteria and/or molds, said method comprising applying to that packing and/or packaging for said foodstuffs, a protective bioactive composition comprising an acid solution having a pH of less than 6 whose acid concentration is from about 0.01% to about 10%; at least one antimicrobial metal ion source partially, or preferably, fully dissolved therein, and, optionally, though preferably, at least one surfactant wherein the acid is present in a molar excess relative to the antimicrobial metal ions and the level of the antimicrobial metal ion in the solution is from about 1 ppm to about 500 ppm, preferably from about 1 to about 300 ppm, more preferably about 2 ppm to about 100 ppm, most preferably from about 5 to about 50 ppm, in the case of a single antimicrobial metal ion and from about 2 ppm to about 1000 ppm, preferably from about 2 ppm to about 500 ppm, more preferably from about 5 ppm to 300 ppm, most preferably from about 5 ppm to about 150 ppm in the case of multiple metal ions. Preferably these compositions will have at least a 2× molar excess, preferably at least a 5× molar excess of the acid relative to the metal ion(s), and a pH of from about 1.5 to about 5, most preferably from about 2 to about 4. Where the acid is other than a mineral acid, the product should have at least one anionic, non-ionic and/or amphoteric surfactant that impacts or interacts with cell wall membranes of microorganisms, especially pathogenic microbes, or the function thereof.

DETAILED DESCRIPTION

The present invention embraces many different embodiments, as set forth above, all of which have significant degree of common characteristics and make-up. Fundamentally, the present invention is centered on the use of a protective bioactive composition comprising one or more sources of antimicrobial metal ions, an acid, and, optionally, though preferably, one or more surfactants, especially surfactants that affect and/or interact with cell walls or membranes of microorganisms, especially pathogenic microbes. These compositions, alone or in combination with conventional bioactive agrichemical actives and formulations, have been found to manifest broad and surprisingly efficacious as well as synergistic bioefficacy.

The protective bioactive composition may exist as solid material, in essence a powder for dusting, henceforth oftentimes referred to as the "bioactive acid composition", or as a liquid, henceforth oftentimes referred to as the "bioactive acid solution" and jointly oftentimes referred to as the "bioactive acid solution or composition". As used herein, the term "bioactive" is intended to include agents that kill or prevent or inhibit the growth and/or proliferation of bacteria, fungi, viruses, and plant, stramenophile and fungi-like protists that are associated with food-borne illnesses and/or are responsible for the spoilage and visual degradation of food crops, including, but not limited to, fruits and vegetables. Finally, the terms "food" and "foodstuff" are intended to encompass and include all food, foodstuff, feed, and feedstuff and the like including fruits, vegetables, nuts, eggs, fish, poultry, meats, and the like.

The acids that may be used in preparing the protective bioactive compositions of the present invention are either solid or liquid in their natural state and are readily soluble or dissolved in or miscible with water or an aqueous based solvent. Alternatively, it is also contemplated that protective bioactive composition may be an oil or other non-aqueous or lipophilic solvent based system. Here, either the components of the protective bioactive composition must be soluble in or miscible with the chosen oil or other non-aqueous or lipophilic solvent or the aqueous or aqueous-based bioactive acid solution is to be combined with the oil or other non-aqueous or lipophilic solvent to form an emulsion or suspension.

Exemplary acids include the organic acids, especially the carboxylic acids such as citric acid, valeric acid, itaconic acid, acetic, citriconic acid, lactic acid, malic acid, succinic acid, aldaric acid, malonic acid, proprionic acid, malonic acid, maleic acid, salicylic acid, glutaric acid, tartaric acids, benzoic acid and the like, as well as the mineral acids such as nitric acid, sulfuric acid, phosphoric acid, boric acid, and the like. The preference is for weaker or moderate acids such as aldaric, citric, malic, and lactic acids as opposed to the moderate to strong mineral acids like boric and phosphoric acids. However, strong acids, especially strong mineral acids like sulfuric or nitric acid, may be used; however, depending upon the strength of the acid, it may be preferable to buffer the acid so as to avoid handling, use and/or consumption problems. This is particularly important pre-harvest protective bioactive compositions since the application of the composition to the plans may damage or kill the plant. It is also important for pre- and post-harvest applications due to possible health concerns associated with the handling of treated food and foodstuffs and the consumption thereof. Thus, while efficacious, it is most preferable to avoid mineral acids and strong acids and, instead, employ carboxylic acids and other weak acids. Additionally, though some suitable acids fall outside of this range, it is desirable that the pKa (in water@25° C.) of the acid be greater than 0, preferably greater than 1, most preferably greater than 1.5.

As noted, acidity is critical to the efficacy of the protective bioactive compositions of the present invention. Generally speaking, the pH of the protective bioactive compositions of the present invention will be less than 6, preferably from about 1.5 to 5 and more preferably from about 2 to about 4, most preferably greater than 2. In the case of assessing or confirming the pH of the solid bioactive acid composition according to the present invention, the bioactive composition is first dissolved in water to a concentration equivalent to that at which it would be applied in use, and the pH measured.

The second critical aspect of the acid concentration relates to the excess molar equivalence of acid to the antimicrobial metal ions present in the protective bioactive compositions. At a minimum, there must be a 2 times molar excess, though preferably there is at least a 5 times, and most preferably at least a 10 times, molar excess acid. These levels are typically attained by formulating bioactive acid solutions whereby the acid concentration in the final diluted state of the bioactive composition is from about 0.01% to about 10%, preferably from about 0.1% to about 4% by weight of the solution. Higher concentrations may also be used, e.g., up to 20% or more, provided that the food, foodstuff or other substrate to which the bioactive composition is to be applied is not adversely affected by the higher acid content and/or the acid is a weak or weakly moderate acid.

The second critical component of the protective bioactive compositions is the antimicrobial metal ion: more aptly its metal ion source. Suitable metal ions are selected from the group consisting antimicrobial transition metal ions and poor ions that have shown antimicrobial bioefficacy. Preferred metal ions are selected from the group consisting of silver, copper, zinc, tin, iron, gold, or iron ions or combinations of any two or more of the foregoing. Most preferably, the metal ions are selected from the group consisting of silver, copper and zinc ions and combinations of any two or all three. Protective bioactive compositions in which at least two and preferably all three of these preferred ions are present are especially beneficial and preferred. Where multiple antimicrobial metal ions are present, each will be present in a molar amount of 3 to 97 percent, preferably 9 to 91 percent, more preferably 20 to 80 percent. In its preferred embodiment, where multiple metal ions are present, they will be present in an equal amount whereby no one metal ion is more than 20 times, more preferably no more than 10 times that of any other metal ion. Especially good results have been found where each antimicrobial metal ion is present in an equal amount, by weight.

The metal ion is added to the acid solution or, as appropriate, the acid, in the form of a source compound, salt or complex that readily releases the ions or otherwise dissociates in the acid solution or when the source and acid are dissolved in a solvent, especially water or a water-based solvent. Exemplary salts and organometallic compounds that may suitably serve as the ion sources include the respective oxides, sulfides, carbonates, nitrates, phosphates, dihydrogen phosphates, sulfates, oxalates, quinolinolates, thiosulfates, sulfonates, phthalates, hydroxides, glycolates, and the like of the antimicrobial metals as well as the carboxylic acid salts thereof, especially the simple carboxylates, such as the citrates, benzoates, acetates, lactates, etc. of said antimicrobial metals. Other salts such as the halide salts and substituted halide salts, such as the halides, hexafluoroantimonates, tetrafluoroborates, and perchlorates of said antimicrobial metals may be used though they are less desirable as they tend to have slow and/or poor solubility, especially in water. Specific metal ion sources include, but are certainly not limited to, silver nitrate, silver oxide, silver acetate, silver citrate, cupric oxide, copper hydroxide, cuprous oxide, copper oxychloride, cupric acetate, copper quinolinolate, copper citrate, zinc oxide, zinc citrate, and the like.

It has also been surprisingly found that certain inorganic complexes may also serve as the metal ion source. Specifically, ion-exchange type antimicrobial agents and dissolving glass antimicrobial agents may be used where the carrier matrix of these materials is soluble in the acid or diluted acid. For example, it has been found that zeolites are readily soluble in concentrated citric acid. Here the metal ion source or sources are added to the acid with mixing until the particles are dissolved. It is also contemplated that these metal ion sources may be only partially dissolved so as to provide for a longer term source of the antimicrobial metal ion. While these ion sources tend to dissolve in the diluted acid, to speed up and/or enhance the dissolving of the metal ion source, it is preferable to dissolve them in a concentrated acid solution, preferably one of from about 40% to 80% concentration.

Suitable ion-exchange type agents include, but are not limited to aluminosilicates, zeolites, hydroxyapatite, and zirconium phosphates, all of which are commercially available and/or fully described in the patent literature. For example, antimicrobial metal ion-containing hydroxyapatite particles are described in, e.g., U.S. Pat. Nos. 5,009,898 and 5,268,174; antimicrobial metal ion-containing zirconium phosphates are described in, e.g., U.S. Pat. Nos. 4,025,608; 4,059,679; 5,296,238; 5,441,717 and 5,405,644 as well as in the Journal of Antibacterial and Antifungal Agents, Vol. 22, No. 10, pp. 595-601, 1994; and antimicrobial metal ion-containing aluminosilicates and zeolites are described in, e.g., U.S. Pat. Nos. 4,911,898; 4,911,899; 4,938,955; 4,938,958; 4,906,464; and 4,775,585, all of the aforementioned patents hereby being incorporated herein by reference in their entirety. Suitable soluble glasses include those described in, e.g., U.S. Pat. No. 5,470,585, which is also incorporated herein by reference in its entirety.

While individual metal ion sources may be used, it is also desirable to use combinations of metal ion sources so as to provide a mixture of metal ions. In certain instances, a single source may provide multiple metal ions. For example, preferred ion-exchange type metal ion sources include AgION AJ10D which contains both silver and zinc ions and AgION AC10D which includes both silver and copper ions. Most preferably, the metal ion sources are the readily soluble salts and compounds, as mentioned above, and most preferably the combination of such compounds whereby solutions having equal or relatively equal concentrations of each of silver, copper and zinc ions are prepared. Suitable combinations include combinations of silver citrate, copper citrate and zinc citrate as well as combinations of silver nitrate, copper sulfate and zinc oxide.

The amount of the antimicrobial metal ion source to be incorporated into the acid solution or, as appropriate, to be combined with the acid is that which is sufficient to provide a concentration of from about 1 ppm to about 500 ppm, preferably from about 1 ppm to about 300 ppm, more preferably about 2 ppm to about 100 ppm, most preferably from about 5 to about 50 ppm of each antimicrobial metal ion, in the bioactive acid solution or bioactive acid composition at its diluted, end-use concentration. Where multiple metal ions and/or metal ion sources are used to provide combinations of metal ions, the total concentration of metal ions in the solutions should be from about 2 ppm to about 1000 ppm, preferably from about 2 ppm to about 500 ppm, more preferably from about 5 ppm to 300 ppm, most preferably from about 5 ppm to about 150 ppm, in the bioactive acid solution or bioactive acid composition at its diluted, end-use concentration. Of course higher levels could be used but are not necessary to provide suitable bioefficacy and, more importantly, such higher use conflicts with the desired intent of minimizing metal addition to the environment. Thus, in following with said objective, it is preferable to use the minimal, or nearly so, amount possible for the desired application.

In pre-harvest applications, phytotoxicity is especially of concern. Thus, in accordance with the agricultural and horticultural applications of this invention, the level of the metals should be less than would otherwise cause phytotoxicity. Most preferably, as noted above, the objective is to use as low a level of metal ion as is reasonably possible yet continue to provide the benefits desired, especially fungicidal, protisticidal, and/or antimicrobial properties. This concern is especially pertinent to those protective bioactive compositions containing copper alone or in combination with one or more of the other antimicrobial metal ions and most especially, where the bioactive acid solution or composition is to contain or be used in conjunction with another copper or copper-based material. In this respect, it should be noted that the aforementioned limitations on the antimicrobial metal ions refers only to those antimicrobial metal ions contributed by the one or more sources of antimicrobial metal ions associated with the bioactive acid solution or bioactive acid composition, and not to the copper or any other antimicrobial metals or metal ions that may be contributed by other compounds or materials to be used in conjunction or in combination with the bioactive acid solutions or bioactive acid compositions.

Optionally, though preferably, the protective bioactive compositions of the present invention include one or more surfactants, especially water soluble surfactants. Although good results have been achieved in weak and moderate acid bioactive acid solutions without the surfactants, the use of the surfactant should be and is generally preferred with such acids. Furthermore, while certain strong and very strong acids, especially mineral acids, do not warrant the need for surfactants, e.g., phosphoric acid, it is especially desirable, and in some instances necessary, e.g., where other than only short term bioefficacy is desired, to employ one or more surfactants. Especially preferred surfactants are those that affect or interact with cell walls or membranes of microorganisms, especially pathogenic microbes, or their function. Suitable surfactants include anionic, cationic, non-ionic and amphoteric (e.g., zwitterionic) surfactants, especially those that are water soluble or show relatively good water solubility. Preferably the surfactants are anionic, non-ionic and/or amphoteric surfactants such as the sulfonates, sulfates, sulfosuccinates, sarcosinates, mono and diglycerides, amine oxides, ether carboxylates, betaines, sulfobetaines, gylcinates and the like. Generally, cationic and those non-ionic surfactants having polyalkylether units, especially polyethylene oxide units, with degrees of polymerization of the alkylene ether unit of greater than about 6 do not show the same level of effectives in providing synergy to the bioactive compositions as the other surfactants. Nonetheless, such surfactants may be used in combination with effective surfactants so long as they do not materially detract from or reduce the bioefficacy of the compositions.

Generally speaking, the surfactant will be present in an amount of from about 0.001% to about 3%, preferably from about 0.01% to about 0.5%, by weight based on the total weight of the protective bioactive composition. While higher loadings could be used, it is not necessary to manifest the desired synergy in bioefficacy. Similarly, while lower loadings could be used, the manifestation of any synergistic or enhanced performance owing to the surfactant is not likely to be seen. Generally, where the surfactant is basic in nature or one that hydrolyzes in water to form a basic solution, the amount should be minimized and/or the amount of acid increased so as to avoid too much neutralization of the bioactive acid solution.

Exemplary anionic surfactants and classes of anionic surfactants suitable for use in the practice of the present invention include: alcohol sulfates; alcohol ether sulfates; alkylaryl ether sulfates; alkylaryl sulfonates such as alkylbenzene sulfonates and alkylnaphthalene sulfonates and salts thereof; alkyl sulfonates; mono- or di-phosphate esters of polyalkoxylated alkyl alcohols or alkylphenols; mono- or di-sulfosuccinate esters of $C_{12}$ to $C_{15}$ alkanols or polyalkoxylated $C_{12}$ to $C_{15}$ alkanols; alcohol ether carboxylates; phenolic ether carboxylates; polybasic acid esters of ethoxylated polyoxyalkylene glycols consisting of oxybutylene or the residue of tetrahydrofuran; sulfoalkylamides and salts thereof such as N-methyl-N-oleoyltaurate Na salt; polyoxyalkylene alkylphenol carboxylates; polyoxyalkylene alcohol carboxylates alkyl polyglycoside/alkenyl succinic anhydride condensation products; alkyl ester sulfates; naphthalene sulfonates; naphthalene formaldehyde condensates; alkyl sulfonamides; sulfonated aliphatic polyesters; sulfate esters of styrylphenyl alkoxylates; and sulfonate esters of styrylphenyl alkoxylates and their corresponding sodium, potassium, calcium, magnesium, zinc, ammonium, alkylammonium, diethanolammonium, or triethanolammonium salts; salts of ligninsulfonic acid such as the sodium, potassium, magnesium, calcium or ammonium salt; polyarylphenol polyalkoxyether sulfates and polyarylphenol polyalkoxyether phosphates; and sulfated alkyl phenol ethoxylates and phosphated alkyl phenol ethoxylates; sodium lauryl sulfate; sodium laureth sulfate; ammonium lauryl sulfate; ammonium laureth sulfate; sodium methyl cocoyl taurate; sodium lauroyl sarcosinate; sodium cocoyl sarcosinate; potassium coco hydrolyzed collagen; TEA (triethanolamine) lauryl sulfate; TEA (Triethanolamine) laureth sulfate; lauryl or cocoyl sarcosine; disodium oleamide sulfosuccinate; disodium laureth sulfosuccinate; disodium dioctyl sulfosuccinate; N-methyl-N-oleoyltaurate Na salt; tristyrylphenol sulphate; ethoxylated lignin sulfonate; ethoxylated nonylphenol phosphate ester; calcium alkylbenzene sulfonate; ethoxylated tridecylalcohol phosphate ester; dialkyl sulfosuccinates; perfluoro ($C_6$-$C_{18}$)alkyl phosphonic acids; perfluoro($C_6$-$C_{18}$)alkyl-phosphinic acids; perfluoro($C_3$-$C_{20}$)alkyl esters of carboxylic acids; alkenyl succinic acid diglucamides; alkenyl succinic acid alkoxylates; sodium dialkyl sulfosuccinates; and alkenyl succinic acid alkylpolyglykosides.

Exemplary amphoteric and cationic surfactants include alkylpolyglycosides; betaines; sulfobetaines; glycinates; alkanol amides of $C_8$ to $C_{18}$ fatty acids and $C_8$ to $C_{18}$ fatty amine polyalkoxylates; $C_{10}$ to $C_{18}$ alkyldimethylbenzylammonium chlorides; coconut alkyldimethylaminoacetic acids; phosphate esters of $C_8$ to $C_{18}$ fatty amine polyalkoxylates; alkylpolyglycosides (APG) obtainable from a acid-catalyzed Fischer reaction of starch or glucose syrups with fatty alcohols, in particular $C_8$ to $C_{18}$ alcohols, especially the $C_8$ to $C_{10}$ and $C_{12}$ to $C_{14}$ alkylpolyglycosides having a degree of polymerization of 1.3 to 1.6, in particular 1.4 or 1.5.

Exemplary non-ionic surfactants and classes of non-ionic surfactants include: polyarylphenol polyethoxy ethers; polyalkylphenol polyethoxy ethers; polyglycol ether derivatives of saturated fatty acids; polyglycol ether derivatives of unsaturated fatty acids; polyglycol ether derivatives of aliphatic alcohols; polyglycol ether derivatives of cycloaliphatic alcohols; fatty acid esters of polyoxyethylene sorbitan; alkoxylated vegetable oils; alkoxylated acetylenic diols; polyalkoxylated alkylphenols; fatty acid alkoxylates; sorbitan alkoxylates; sorbitol esters; $C_8$ to $C_{22}$ alkyl or alkenyl polyglycosides; polyalkoxy styrylaryl ethers; alkylamine oxides; block copolymer ethers; polyalkoxylated fatty glyceride; polyalkylene glycol ethers; linear aliphatic or aromatic polyesters; organo silicones; polyaryl phenols; sorbitol ester alkoxylates; and mono- and diesters of ethylene glycol and mixtures thereo; ethoxylated tristyrylphenol; ethoxylated fatty alcohol; ethoxylated lauryl alcohol; ethoxylated castor oil; and ethoxylated nonylphenol; alkoxylated alcohols, amines or acids, mixtures thereof as well as mixtures thereof with diluents and solid carriers, in particular clathrates thereof with urea. The alkoxylated alcohols, amines or acids are preferably based on alkoxy units having 2 carbon atoms, thus being a mixed ethoxylate, or 2 and 3 carbon atoms, thus being a mixed ethoxylate/propoxylated, and having at least 5 alkoxy moieties, suitably from 5 to 25 alkoxy moieties, preferably 5 to 20, in particular 5 to 15, in the alkoxy chain. The aliphatic moieties of the amine or acid alkoxylated may be straight chained or branched of 9 to 24, preferably 12 to 20, carbon atoms. The alcohol moiety of the alcohol alkoxylates is as a rule derived from a $C_9$-$C_{18}$ aliphatic alcohol, which may be non-branched or branched, especially monobranched. Preferred alcohols are typically 50% by weight straight-chained and 50% by weight branched alcohols.

As noted above, the aforementioned surfactants may be used alone or in combination. Furthermore, while not all of the surfactants mentioned above will provide the desired synergy to the protective bioactive compositions, they may nevertheless be used in combination with the synergistic surfactants for their intended function. For example, certain of the aforementioned surfactants may enhance the dispersion of the actives in the solvent or may enhance the wetting out of the food or foodstuff to which the inventive bioactive compositions of the present invention are applied. All of these surfactant materials are well known and commercially available. Furthermore, those skilled in the art, without undue experimentation, will readily appreciate which surfactants and/or combinations of surfactants, in addition to the synergist surfactants, may be used for the specific end-use application. Again, it is important that when additional surfactants are employed for other purposes they not interfere with or have minimal interference with the synergy that results from the desired surfactants, i.e., those that show synergy in providing antimicrobial, including antibacterial and/or antifungal, activity when used in combination with the acid and metal ions.

If any interference exists and the other surfactant is necessary or otherwise desired for the application, then its use should be minimized to produce the least adverse impact on the synergy and/or attributes of the protective bioactive compositions. Furthermore, if there is concern with such interference, especially if the surfactants are used or to be used in an amount that will neutralize the acid of the bioactive compositions so as to render them outside of the claimed range, then those surfactants may still be added but not until the time of application. In essence the protective bioactive compositions of the present inventions may be employed as two- or more part systems to be mixed when applied. Most preferably, it is best to avoid the use of such surfactants or those amounts of said surfactants that will adversely affect the bioefficacy of the claimed compositions.

The protective bioactive compositions of the present invention may be used alone or in conjunction with or in combination with one or more other conventional agents or actives for food and foodstuff protection and/or preservation. In light of their synergy with general antifungal agents, it is likewise anticipated that such combinations will manifest a marked and synergistic enhancement to shell life and reduction in spoilage. In following, it is believed that previously non-efficacious levels of conventional protective actives may be rendered efficacious as a result of the presence of the bioactive acid solution or composition. Similarly, it is believed that these combinations will enable one to achieve the same level of bioefficacy with less than the conventional application rates or amounts of the conventional bioactive agrichemical active. Additionally, and of particular significance, the combination is also believed to reduce the incidence of and/or the speed with which bio-resistance to conventional protective agents and formulations, especially the synthetic organic agrichemicals, is manifested in target organisms. Thus, the commercial life expectancy of these and future conventional agrichemical actives is likely to be increased and the generation of superbugs or resistant strains of the bacterial fungi, protists and the like decreased or delayed.

The protective bioactive compositions according to the present invention can be used alone or, preferably and advantageously, they are used in combination with (typically as a mixture) one or more other compatible components or additives typical of pre- and post-harvest protective compositions and treatments, including, for example, solid or liquid fillers or diluents, adjuvants, surfactants or equivalents, which are suitable for the desired use and which are acceptable for use, from an environmental, health and safety as well as regulatory perspective. In following, the formulations can also contain ingredients of other types, such as protective colloids, adjuvants, binders, rain fasteners, thickeners, thixotropic agents, penetrating agents, oils for spraying, stabilizers, antifreeze agents, defoaming agents, foaming agents, corrosion inhibitors, dyes, or the like, as well as other known active ingredients which have food protective, e.g., antifungal, antibacterial and antiviral properties, or which otherwise slow down the food maturation and ripening process.

The nature and amount of the additives to be employed in the protective bioactive compositions of the present invention depends, in part, upon when it is to be applied, how it is to be applied and the products or foods or foodstuffs to which it is to be applied. For example, the protective bioactive compositions may be in the form of and/or manufactured into e.g. solutions, oil in water emulsions, wettable powders, soluble powders, suspensions, dusts, dispersible granules, microcapsules, gels, tablets and other formulation types by well-established procedures. Similarly, the method of application such as spraying, atomizing, dispersing, dusting, dipping, coating, and the like may be chosen based on the nature of the compositions to be applied, when it is to be applied, e.g., pre- or post-harvest or to the packing or packaging, etc., and the food or foodstuff to which it is to be applied.

Although the typical definition of "filler" is a material added for the primary purpose of adding bulk, in the present application, "fillers" typically have function and utility and generally refer to organic or inorganic, natural or synthetic components with which the active components are combined to facilitate their application, for example, in pre-harvest application to the plants, trees, vines and the like. These fillers are generally inert and must be acceptable for the intended application, especially for agronomic uses, in particular for treating plants.

The filler can be solid, for example clays, natural or synthetic silicates, silica, resins, waxes, solid fertilizers (for example ammonium salts), natural soil minerals, such as kaolins, clays, talc, lime, calcium carbonate, quartz, attapulgite, montmorillonite, bentonite or diatomaceous earths, or synthetic minerals, such as silica, alumina or silicates, in particular aluminium or magnesium silicates. The solid fillers which are suitable for granules are as follows: natural, crushed or broken rocks, such as calcites, marble, pumice, sepiolite or dolomite; synthetic granules of inorganic or organic flours; granules of organic material such as sawdust, coconut shell, corn ear or envelope, or tobacco stem; kieselguhr, tricalcium phosphate, powdered cork or adsorbent carbon black; water-soluble polymers, resins, waxes; or solid fertilizers. Such compositions can, if so desired, contain one or more compatible agents such as wetting agents, dispersing agents, emulsifiers or dyes which, when they are solid, can also act as diluents. Where the additives are alkaline and will likely increase the pH of the compositions, e.g., talc, lime, calcium carbonate, and marble, the amount by which they are added should not cause the pH to exceed the claimed ranges or additional acid should be added to maintain the desired pH. Preferably, such materials should be avoided altogether.

The fillers can also be liquids, for example: water, alcohols, in particular butanol or glycol, as well as ethers or esters thereof, in particular methyl glycol acetate; ketones, in particular acetone, cyclohexanone, methyl ethyl ketone, methyl isobutyl ketone or isophorone; petroleum fractions such as paraffinic or aromatic hydrocarbons, in particular xylenes or alkylnaphthalenes; mineral or plant oils; aliphatic chlorohydrocarbons, in particular trichloroethane or methylene chloride; aromatic chlorohydrocarbons, in particular chlorobenzenes; water-soluble or highly polar solvents such as dimethylformamide, dimethyl sulphoxide, N,N-dimethylacetamide or N-methylpyrrolidone; N-octylpyrrolidone, liquefied gases; or the like, whether they are taken separately or as a mixture.

As mentioned above, depending upon the end-use application, the inventive protective bioactive compositions will contain one or more additional surfactants (additional to the surfactant(s) that are optionally part of the bioactive acid solution or bioactive acid composition) as emulsifiers, dispersing agents, wetting agents and the like. These additional surfactants may be cationic, anionic, nonionic or amphoteric surfactants or mixtures of these surfactants. Among those surfactants which are used, for example, are polyacrylic acid salts, lignosulphonic acid salts, phenolsulphonic or naphthalenesulphonic acid salts, polycondensates of ethylene oxide with fatty alcohols or fatty acids or fatty esters or fatty amines, substituted phenols (in particular alkylphenols or arylphenols), ester-salts of sulphosuccinic acid, taurine derivatives (in particular alkyl taurates), phosphoric esters of alcohols or of polycondensates of ethylene oxide with phenols, fatty acid esters with polyols, or sulphate, sulphonate or phosphate functional derivatives of the foregoing compounds as well as those surfactants described above relative to the synergistic surfactant for the bioactive acid solution or composition. Here, however, the surfactants are generally present at much higher concentrations versus that needed to show synergy with respect to the acid/metal combination. The presence of at least one additional surfactant is generally essential when the active materials and/or the inert filler are insoluble or only sparingly soluble in water and when the filler for the said composition to be applied is water. For foliar applications, the choice of surfactants is oftentimes paramount for obtaining good wetting of the food or foodstuff surface and, hence, bioavailability of the active material(s); thus, a combination of a surfactant of hydrophilic nature (HLB>10) and a surfactant of lipophilic nature (HLB<5) will preferably be used.

Generally, when the protective bioactive composition is to be applied directly to the food or foodstuff, the composition will include a binder, rain fastener, or other adhesive type components for ensuring long-term adherence of the bioactive materials to the food or foodstuff surface. Suitable binders are well known in include, e.g., water-soluble and water-dispersible film-forming polymers. Suitable polymers have an average molecular weight of at least about 1,000 up to about 100,000; more specifically at least about 5,000, up to about 100,000. Those protective bioactive compositions based on a bioactive acid solution generally contain from about 0.5% to about 10%, preferably from about 1.0% to about 5%, by weight of the composition of the binder, film-forming polymer, and the like. Suitable film-forming polymers include, but are not limited to a) alkyleneoxide random and block copolymers such as ethylene oxide-propylene oxide block copolymers (EO/PO block copolymers) including both EO-PO-EO and PO-EO-PO block copolymers; ethylene oxide-butylene oxide random and block copolymers, $C_2$-$C_6$ alkyl adducts of ethylene oxide-propylene oxide random and block copolymers, $C_2$-$C_6$ alkyl adducts of ethylene oxide-butylene oxide random and block copolymers; b) polyoxyethylene-polyoxypropylene monoalkylethers such as methyl ether, ethyl ether, propyl ether, butyl ether or mixtures thereof; c) vinylacetate/-vinylpyrrolidone copolymers, d) alkylated vinylpyrrolidone copolymers, e) polyvinylpyrrolidone, and f) polyalkyleneglycol including the polypropylene glycols and polyethylene glycols. Specific examples of suitable polymers include Pluronic P103 (BASF) (EO-PO-EO block copolymer), Pluronic P65 (BASF) (EO-PO-EO block copolymer), Pluronic P108 (BASF) (EO-PO-EO block copolymer), Vinamul 18160 (National Starch) (polyvinylacetate), Agrimer 30 (ISP) (polyvinylpyrrolidone), Agrimer VA7w (ISP) (vinyl acetate/vinylpyrrolidone copolymer), Agrimer AL 10 (ISP) (alkylated vinylpyrrolidone copolymer), PEG 400 (Uniqema) (polyethylene glycol), Pluronic R 25R2 (BASF) (PO-EO-PO block copolymer), Pluronic R 31R1 (BASF) (PO-EO-PO block copolymer) and Witconol NS 500LQ (Witco) (butanol PO-EO copolymer).

Additional adhesive and adhesive type materials that may be used include carboxymethylcellulose, or natural or synthetic polymers in the form of powders, granules or matrices, such as gum arabic, latex, polyvinylpyrrolidone, polyvinyl alcohol or polyvinyl acetate, natural phospholipids, such as cephalins or lecithins, or synthetic phospholipids can be used in the formulations.

It may also be desirable to thicken the protective bioactive compositions, especially where there is concern that the composition will quickly run off or run down food or foodstuff to which it is applied and/or where it is desirable to "thicker" coating of the composition on the surface of the food or foodstuff. Suitable thickeners include water-soluble polymers which exhibit pseudoplastic and/or thixotropic properties in an aqueous medium such as gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate salt, polyacrylamide, alkali metal salts of the maleic anhydride copolymers, alkali metal salts of poly (meth)acrylate, and the like. As suitable thickeners, including thixotropes, there may also be mentioned attapulgite-type clay, silica, fumed silica, carrageenan, croscarmellose sodium, furcelleran, glycerol, hydroxypropyl methylcellulose, polystyrene, vinylpyrrolidone/styrene block copolymer, hydroxypropyl cellulose, hydroxypropyl guar gum, and sodium carboxymethylcellulose. Xanthan gum is preferred.

In the case of bioactive agrichemical compositions that are or may be subject to freezing during storage or use, especially aqueous and aqueous-based concentrates and solutions, it is desirable to add antifreeze additives. Specific examples of suitable antifreezes include ethanol, 1,2-propylene glycol, 1,3-propylene glycol, 1,2-butanediol, 1,3-butanediol, 1,4-butanediol, 1,4-pentanediol, 3-methyl-1,5-pentanediol, 2,3-dimethyl-2,3-butanediol, trimethylol propane, mannitol, sorbitol, glycerol, pentaerythritol, 1,4-cyclohexanedimethanol, xylenol, bisphenols such as bisphenol A or the like. In addition, ether alcohols such as diethylene glycol, triethylene glycol, tetraethylene glycol, polyoxyethylene or polyoxypropylene glycols of molecular weight up to about 4000, diethylene glycol monomethylether, diethylene glycol monoethylether, triethylene glycol monomethylether, butoxyethanol, butylene glycol monobutylether, dipentaerythritol, tripentaerythritol, tetrapentaerythritol, diglycerol, triglycerol, tetraglycerol, pentaglycerol, hexaglycerol, heptaglycerol, octaglycerol and the like. As a particular subset of suitable antifreeze materials there can be mentioned ethanol, propylene glycol and glycerin.

It is possible to use dyes such as inorganic pigments, such as, for example: iron oxides, titanium oxides, Prussian blue; organic dyestuffs, such as those of the alizarin, azo or metal phthalocyanin type; or of trace elements such as iron, manganese, boron, copper, cobalt, molybdenum or zinc salts. The use of such dyes enables one to determine which areas and substrates, including plants, have been treated with the bioactive composition. Such marking is especially important for a pre-harvest application, especially aerial, drop or broadcast application as it enables the pilot or driver of the dispensing vehicle see what areas have already been treated.

Although not all additives and adjuvants have been described above, those skilled in the art, particularly in the art pertinent to the specific end-use application anticipated, will certainly appreciate what other ingredients, additives and the like would or should be used for their application. By the same token, those skilled in the art will readily appreciate that many of the aforementioned acids, antimicrobial metals, surfactants and other additives mentioned, e.g., ethylene glycol anti-freeze additives, are inappropriate for human consumption, if not animal consumption. Thus, it is to be appreciated that the extent of the present invention pertains to those compositions that can be applied safely and are acceptable for human and/or animal consumption. In this respect, it is also to be appreciated that certain components may be suitable for human and/or animal consumption at certain concentrations or following a specified period of time and, hence, those materials and the inventive protective bioactive containing them are within the intended scope of the present invention.

The amount by which each additive is to be incorporated into the protective bioactive compositions will, once again, depend upon the end-use application and the method of application and environment into which it is to be employed. Generally, though, the selection and amount is that which is conventional for such additives in such applications. However, with the selection of any additives, it is important to ensure that they will not interfere with the bioactivity of the compositions of the present invention or that any such interference will be minimized so as to enable one to take the most advantage of the protective bioactive compositions of the present invention. Those skilled in the art, based upon the teachings set forth herein and in the following examples, will appreciate where attention is due and, in any event, such can be addressed by simple screening applications.

As noted above, it is important to avoid the use of conventional bioactive agrichemical actives as well as any other additives and components, including those of the types mentioned above, that interfere with or adversely affect the bioefficacy of the compositions according to the present invention. Most especially, it is important to avoid the use of those agrichemical actives and other additives or compounds that are known to or will likely irreversibly or strongly sequester, bind, or complex with the antimicrobial metal ions in solution. In following, not intending to be bound by theory, it is believed that retention of the antimicrobial metal ionic charge is important for maintaining bioefficacy. For example, it is best to avoid the use of ammonium salts such as ammonium sulphate, ammonium chloride, ammonium citrate, ammonium phosphate. To the extent any such materials are present or to be used, their use or, more accurately, the amount thereof, should be minimized and/or the metal ion concentration increased to offset the loss of free ions in solution compounds.

The protective bioactive compositions of the present invention may be made by any known method for formulating agrichemical compositions, especially antimicrobial and antifungal type compositions. Generally speaking, whether making a liquid system or a solid system, the bioactive acid solution or, if applicable, the solid bioactive acid composition is prepared before the addition of a conventional bioactive active or formulation and/or other conventional agrichemical additives and agents, all as discussed above.

The bioactive acid solution may be prepared in a number of conventional ways. For example, each component may be dissolved in the appropriate solvent, most notably water or a water-based solvent, and the solutions combined in the appropriate proportions. To some extent, the sequence of the addition and whether a pre-concentrate of the acid in the solvent is formed depends upon the solubility of the solids themselves. Preferably, the acid is initially dissolved in the appropriate solvent to the desired concentration. Where one is intending to first form a concentrate to be let down for application, the amount of acid to be dissolved in the solvent should be such that the acid concentration is at least 40 percent and preferably form 40 to 80 percent. The antimicrobial metal ion source or sources are then dissolved in the concentrated acidic solution. The use of a concentrated acid solution is also beneficial where the antimicrobial metal source is more readily dissolved or soluble in the concentrated acid solution as opposed to fully diluted acid solution or water. For example, as mentioned above, where the metal ion source is an antimicrobial metal ion containing ion-exchange type agent, especially those whose core is a zeolite, the use of concentrated acids has been found to readily dissolve the zeolite. Thereafter, the concentrated solution is merely diluted with the appropriate liquid diluent, typically water or an aqueous based diluent, most typically water, to the desired concentration after the solids are dissolved.

Where there is difficulty in dissolving the antimicrobial metal source or sources in the concentrated or dilute acid solution, or the rate is undesirably slow, the antimicrobial metal ion source or sources may first be dissolved in water or another suitable aqueous-based solvent and that combined with the formed acid solution. Here, the acid solution is preferably of a higher concentration than intended in the protective bioactive composition so as to account for the dilution upon adding the dissolved antimicrobial metal ion source or sources.

Similarly, it may be desirable to make individual stock solutions of each of the components of the bioactive acid solution which stock solutions are then combined in the appropriate proportions. Again, the concentration of each stock solution would be tailored to account for the dilution upon their combination.

In each of the foregoing instances, the solvent/solutions may be heated and are preferably agitated to enhance the solubility/expedite the dissolving of the solids in the liquid system. Furthermore, while the dissolution of antimicrobial metal ion source or sources is perhaps the simplest and most cost effective method of the preparation of the bioactive acid solutions, these bioactive acid solutions may also be prepared by, e.g., electrolytically generating the metal ion in acid solutions as seen in Arata et. al. (U.S. Pat. No. 6,197,814; US 2003/0198689A1, US 2003/0178374A1; US2005/0245605A1 and US2006/0115440A1, all of which are incorporated herein by reference in their entirety) or by high temperature and pressure as seen in Cummins et. al. (U.S. Pat. No. 7,192,618, incorporated herein be reference).

The surfactants may be added to the bioactive acid solution or the concentrate or may be added concurrent with or subsequent to the combination of the bioactive acid solution with the conventional bioactive agrichemical composition.

Flowable solid protective bioactive compositions may also be made in a number of ways. For example, the acid, the antimicrobial metal ion source or sources, a solid filler or diluent, and, if present, the surfactant can be dry blended. Dry blending is still possible even if the surfactant or one of the surfactants is a liquid since the amount employed is so low and will be adsorbed or absorbed by the dry materials. Alternatively, if one wanted to make a concentrate that is subsequently let down for application, one may simply omit or reduce the amount of the solid filler or diluent when preparing the dry blend. At the time of use, this concentrated dry blend is then let down with the solid filler or diluent to the desired end-use concentration.

While dry blending is the easiest manner to form the solid bioactive acid composition concentrate mentioned above, this can also be prepared by forming a highly concentrated bioactive acid solution using a volatile solvent, e.g., water or a water-base solvent, and then allowing the solvent to evaporate to leave the solid material. As necessary, the solid material is then crushed or ground to form small particles, powder or granules, of the solid bioactive acid composition.

The solid protective bioactive compositions may also be prepared by treating a solid filler or diluent material with a concentrated or somewhat concentrated bioactive acid solution. Here the liquid bioactive acid solution is applied to or combined with the filler material, which is preferably in particle form, and is adsorbed by and/or absorbed by the particles of the filler. For example, a mist of the bioactive acid solution may be sprayed or a steady or intermittent stream of the bioactive acid solution may be poured onto the particles as they are tumbled, stirred, etc. Where a conventional active of formulated active in particle form is also present in the protective bioactive composition, it is also contemplated that those particles or a portion thereof may be similarly treated with the bioactive solution and employed instead of or in addition to the aforementioned solid filler or diluent.

Given the high transportation costs and the ease of dilution, it is most preferable and cost effective to prepare concentrates, especially liquid concentrates, of the inventive protective bioactive compositions which concentrates are then diluted or let down at the time of application. These liquid concentrates are then diluted or let down with an appropriate solvent, especially water or a water based solvent, to the desired concentration for application.

Surprisingly, the protective bioactive compositions show a marked bioefficacy even at such low levels of antimicrobial metal ion. This is especially desirable as it avoids or certainly lessens concerns with respect to phytotoxicity, a consequence that can kill the plant and/or alter the visual impression of the food or crop being treated. Additionally, it greatly reduces the amount of metals released to the environment, particularly in the case of pre-harvest applications, as well as from the cleaning of any application apparatus and tanks as well as releases occurring when the treated food or foodstuff is washed before consumption. In this respect, recent water purity investigations have shown detectable levels of various pharmaceutical agents in drinking water supplies that are believed to be attributed to the disposal of expired prescriptions by consumers down their drains. While agrichemicals, heavy metals and the like have long been detected in drinking water, they have typically been attributed to in-field application and industrial disposal; however, in light of the foregoing with respect to pharmaceuticals, it only stands to reason that an additional contamination route is the washing of foods and foodstuffs treated with those agents. Furthermore, the protective bioactive compositions of the present invention do not, or are much less likely to, induce or lead to the manifestation of bioresistance in the targeted organisms: a growing happenstance with organic agents, which, while bothersome at the present time, could lead to catastrophic results if unchecked.

Typically, the rate of application of the inventive bioactive agrichemical compositions of the present invention for pre-harvest applications is such that the total amount of antimicrobial metal ions (as metal) originated from the dissolved antimicrobial metal ion source or sources applied per acre will be about 200 grams or less, preferably 100 grams or less, more preferably 50 grams or less, most preferably 20 grams or less. Of course the specific application rate and, thus, the total amount applied per acre, will vary from target organism to target organism, from one form to another and from one application method to another. Indeed, suitable rates may be such that the total metal ion (as metal) may be on the order of 5 grams per acre, even on the order of fractions of a gram per acre, perhaps as low as 0.5 grams per acre or even 0.05 grams per acre. While higher loadings, higher than 200 grams per acre, may provide even greater or faster bioefficacy, the trade-off of increased environmental, health and safety concerns does not generally warrant or is not typically justified by the increased, oftentimes nominal increase, in bioefficacy. Otherwise, for direct application to the food or foodstuff or to the packing or packaging, the protective bioactive composition of the claimed concentrations and constituents is applied to fully coat or wet the substrate to be treated or the same is dipped in the solution.

The protective bioactive compositions may be applied to any food, foodstuff, feed or feedstuff. Pre-harvest in-field applications may be made to fruiting trees, vegetable crops, feed crops and the like. Similarly, they may be applied as a post-harvest application to the harvested crops including soy beans, tomatoes, potatoes, apples, pears, peaches, grapes, beets, carrots, lettuce, spinach, kale, sugar beets, squashes, melons, peppers, citrus, and the like. They may also be applied to protein and other foods and foodstuffs including eggs, poultry, meats, fish, and the like.

Alternatively, the protective bioactive compositions may be applied to the packing or packaging in which such products and crops are stored, shipped, or sold. Here the packing or packaging material is treated, e.g., sprayed, coated, or saturated, with the bioactive acid solution and allowed to dry. Additionally, the solid bioactive compositions may be incorporated into the packing or packaging material during its manufacture. Finally, it is also contemplated that the protective bioactive composition may be incorporated into ice in which the food or foodstuff is to be packed.

Bioefficacy of the protective bioactive compositions and methods of the present invention is evidenced by an increase in the storage-life or shelf-life of the food treated or exposed to the compositions. Any delay in spoilage and aging, especially a delay of even a day or two, especially five or more days, particularly in the case of fruits and vegetables, is significant, particularly from an economic standpoint. Such is true even if the result is not across the board for the whole of the treated crop. In essence, even a 10% improvement in salable product can have a significant economic impact on growers, wholesalers, food service providers and retailers. The compositions and methods of the present invention provide and are anticipated to provide even better improvements in salable products, up to 25% or more, preferably 50% or more. Where there is particular concern for food-borne human pathogens, then it is most desirable that the protective bioactive compositions provide log kill performance, especially at least a two log kill (99%), if not greater.

The following examples are presented as demonstrating the bioefficacy of the bioactive agrichemical compositions according to the present invention as well as the unexpected synergy resulting from the use of certain surfactants and/or other conventional bioactive agrichemical actives and formulated actives. These examples are merely illustrative of the invention and are not to be deemed limiting thereof. Those skilled in the art will recognize many variations that are within the spirit of the invention and scope of the claims.

Saccharomycetes Cerevisiae Studies

A series of experiments (Examples 1-269 below) were conducted to evaluate the performance of the individual components of the claimed bioactive compositions as well as various combinations thereof, including, the claimed compositions themselves, in suppressing the growth of *Saccharomycetes Cerevisiae* (Fleishmann's Bakers yeast). *Saccharomycetes Cerevisiae* was selected as a test organism as it is generally accepted in the industry as an indicator or surrogate organism for a wide variety of molds and fungi. In each of these experiments, the same general procedure was followed unless otherwise indicated.

Experimental Detail: A growth medium was prepared by adding 10 grams of nutrient medium (Difco Sabouraud dextrose broth from BD of Franklin Lakes, N.J., USA) to 300 ml of distilled water. Fleishmann's Bakers yeast was then added to the growth medium while mixing using a magnetic stirrer until a uniform dispersion was obtained having an initial turbidity of between about 50 and 100 NTU as measured using a HF Instruments DRT 100B Turbidity Meter. Once the appropriate dispersion was obtained, 20 ml aliquots were then dispensed, with continued mixing, into 40 ml borosilicate glass vials with Teflon lined caps (VWR International Cat. No. 15900-004). The system/component to be evaluated was then added to the vial and intimately shaken to ensure a good, substantially homogeneous mixture. The turbidity of each mixture was then determined and the vial transferred to an incubator at 30° C. Each vial was periodically removed from the incubator and the mixture in the vials assessed for turbidity: the specific timing for such evaluation was as set forth in the discussion of the experiments and the accompanying tables.

In each experiment, unless otherwise specified, a 2 ml aqueous solution containing the specified bioactive system or component thereof was added to the 20 ml yeast suspension and mixed thoroughly. Typically the surfactants were added separately in a concentrated solution in water; however, the volume added was negligible: a fraction of an ml. For convenience in understanding efficacy levels, the amounts or concentrations of the various components presented in each of the following tables and experiments are of the diluted material in the test vial: not of the concentrate added to the test vial. Furthermore, the concentrations presented are on the basis of a 20 ml total volume, not the actual 22+ ml volume. Multiplying each of the listed concentrations by 0.9 (or 0.95 with those compositions using 1 ml aqueous solutions) will provide a more accurate assessment of the concentrations of the various components evaluated, i.e., a 5 ppm silver concentration is actually closer to 4.5 ppm. Finally, for those vials to which no bioactive system or component thereof was added (the controls) or which only contained the surfactants, 2 ml of additional growth medium was added to ensure relative equivalent dilutions of the yeast.

In the tables below, the results are presented as the actual turbidity readings (NTU) with a sub-table presenting the change or delta in NTU values. Given the nature of the system, changes in turbidity are reflective of the relative performance/bioefficacy of the bioactive systems and their components. In certain instances, a high level of bioactive material, especially the metal component, caused an immediate and relatively sharp increase in optical density or turbidity. This was believed to have been a result of lysing of at least a portion on the yeast cells themselves. Consequently, especially in those examples having a high level of bioactive, it is equally, if not more, important to look at the change in turbidity from either the half hour or one hour turbidity results, if presented, forward, not from time zero.

Examples 1-21

Acid Concentration

A first series of experiments was conducted for evaluating the performance of various antimicrobial metals and combinations of such metals, with and without citric acid and with and without sodium lauroyl sarcosinate anionic surfactant. Each of the metals was added in the form of an aqueous solution of their citrate salts, namely, silver citrate, copper citrate and zinc citrate, or, in the case of Examples 16-19, as a mixture of all three citrate salts (MI1). The specific formulations evaluated and the resultant yeast growth study results are shown in Tables 1 and 1A.

As seen in Tables 1 and 1A, those formulations having both the acid and the anionic surfactant provided marked yeast growth inhibition through at least the first 24 hour period, even with the low lever of anionic surfactant. Those samples with just the metal ion or the metal ion in combination with the acid had no appreciable effect on yeast growth. Although some inhibition was also noted in those samples wherein only the metal(s) and surfactant were present, the inhibition was not appreciable. Rather, as noted, the further presence of excess acid gave a marked and unexpected level of improvement. Finally, that formulation having all three antimicrobial metal ions, plus the acid and surfactant provided continued to show excellent yeast growth inhibition even at the 96 hour test limit.

Examples 22-42

Surfactant Evaluation

A similar series of experiments was conducted again to evaluate the performance of various combinations of the components of the bioactive

TABLE 1

| Example | Metal Ion and Amount (ppm) | Citric Acid (wt %) | Na Lauroyl Sarcosinate (wt %) | Turbidity (NTU) | | | | |
|---|---|---|---|---|---|---|---|---|
| | | | | Time zero | Time 1 Hr | T 18 hours | T 24 hours | T 96 Hours |
| 1 | Ag 5 ppm | 0 | | 44.5 | 59.6 | 890 | 932 | 995 |
| 2 | Ag 5 ppm | 1 | | 47.5 | 64 | 882 | 902 | 1044 |
| 3 | Ag 5 ppm | 2 | | 50.9 | 68.4 | 881 | 950 | 1025 |
| 4 | Ag 5 ppm | 0 | 0.005 | 46.8 | 51.5 | 596 | 677 | 673 |
| 5 | Ag 5 ppm | 1 | 0.005 | 59.4 | 68.4 | 85 | 130 | 854 |
| 6 | Ag 5 ppm | 2 | 0.005 | 70.9 | 75 | 85 | 120 | 880 |
| 7 | Zn 5 ppm | 0 | | 43.8 | 64.5 | 992 | 993 | 1051 |
| 8 | Zn 5 ppm | 1 | | 46.6 | 66.5 | 934 | 962 | 1027 |
| 9 | Zn 5 ppm | 2 | | 49.5 | 71 | 936 | 1038 | 1063 |

TABLE 1-continued

| Example | Metal Ion and Amount (ppm) | Citric Acid (wt %) | Na Lauroyl Sarcosinate (wt %) | Turbidity (NTU) Time zero | Time 1 Hr | T 18 hours | T 24 hours | T 96 Hours |
|---|---|---|---|---|---|---|---|---|
| 10 | Zn 5 ppm | 0 | 0.005 | 45.9 | 63 | 656 | 747 | 712 |
| 11 | Zn 5 ppm | 1 | 0.005 | 57 | 71 | 160 | 223 | 744 |
| 12 | Zn 5 ppm | 2 | 0.005 | 73 | 76.5 | 105 | 119 | 466 |
| 13 | Cu 5 ppm | 0 | | 45.6 | 68 | 940 | 1021 | 1100 |
| 14 | Cu 5 ppm | 1 | | 49 | 72 | 940 | 1018 | 1102 |
| 15 | Cu 5 ppm | 2 | | 49 | 74 | 900 | 973 | 1100 |
| 16 | MI1 | 0 | 0.005 | 39 | 44.5 | 449 | 575 | 658 |
| 17 | MI1 | 1 | 0.005 | 73.9 | 87 | 100 | 105 | 732 |
| 18 | MI1 | 2 | 0.005 | 132 | 137 | 137 | 137 | 690 |
| 19 | MI1 | 1 | 0.01 | 74.5 | 74.8 | 87 | 89 | 116 |
| 20 | Control (No Biocide) | | | 53.2 | 69.4 | 1031 | 1085 | 1122 |
| 21 | Control (No Biocide) | | | 53.2 | 78 | 1101 | 1093 | 1128 |

* MI1 a 4% citric acid solution containing of 50 ppm each of Ag, Cu and Zn per ml giving ~5 ppm of each in the test vial

TABLE 1A

| Example | Metal Ion and Amount (ppm) | Citric Acid (wt %) | Na Lauroyl Sarcosinate (wt %) | Change in Turbidity from $T_0$ (delta NTU) Time 1 Hr | T 18 hours | T 24 hours | T 96 Hours |
|---|---|---|---|---|---|---|---|
| 1 | Ag 5 ppm | 0 | | 15.1 | 845.5 | 887.5 | 950.5 |
| 2 | Ag 5 ppm | 1 | | 16.5 | 834.5 | 854.5 | 996.5 |
| 3 | Ag 5 ppm | 2 | | 17.5 | 830.1 | 899.1 | 974.1 |
| 4 | Ag 5 ppm | 0 | 0.005 | 4.7 | 549.2 | 630.2 | 626.2 |
| 5 | Ag 5 ppm | 1 | 0.005 | 9 | 25.6 | 70.6 | 794.6 |
| 6 | Ag 5 ppm | 2 | 0.005 | 4.1 | 14.1 | 49.1 | 809.1 |
| 7 | Zn 5 ppm | 0 | | 20.7 | 948.2 | 949.2 | 1007.2 |
| 8 | Zn 5 ppm | 1 | | 19.9 | 887.4 | 915.4 | 980.4 |
| 9 | Zn 5 ppm | 2 | | 21.5 | 886.5 | 988.5 | 1013.5 |
| 10 | Zn 5 ppm | 0 | 0.005 | 17.1 | 610.1 | 701.1 | 666.1 |
| 11 | Zn 5 ppm | 1 | 0.005 | 14 | 103 | 166 | 687 |
| 12 | Zn 5 ppm | 2 | 0.005 | 3.5 | 32 | 46 | 393 |
| 13 | Cu 5 ppm | 0 | | 22.4 | 894.4 | 975.4 | 1054.4 |
| 14 | Cu 5 ppm | 1 | | 23 | 891 | 969 | 1053 |
| 15 | Cu 5 ppm | 2 | | 25 | 851 | 924 | 1051 |
| 16 | MI1 | 0 | 0.005 | 5.5 | 410 | 536 | 619 |
| 17 | MI1 | 1 | 0.005 | 13.1 | 26.1 | 31.1 | 658.1 |
| 18 | MI1 | 2 | 0.005 | 5 | 5 | 5 | 558 |
| 19 | MI1 | 1 | 0.01 | 0.3 | 12.5 | 14.5 | 41.5 |
| 20 | Control (No Biocide) | | | 16.2 | 977.8 | 1031.8 | 1068.8 |
| 21 | Control (No Biocide) | | | 24.8 | 1047.8 | 1039.8 | 1074.8 |

* MI1 a 4% citric acid solution containing of 50 ppm each of Ag, Cu and Zn per ml giving ~5 ppm of each in the test vial compositions of the present invention as well as to demonstrate other anionic surfactants and combinations of surfactants. The specific formulations evaluated and the yeast growth results are presented in Tables 2 and 2A.

Once again, the importance of all three constituents was evident from the results shown in Tables 2 and 2A. These results further confirm that even a low excess acid content, here 0.4%, provides excellent inhibition in yeast growth through 96 hours. The somewhat less than ideal results shown in Examples 26 and 29 suggest some variation amongst anionic surfactants, at least with sodium lauryl sulfate (SLS), with zinc and copper ions. However, the results are still significantly better than without a surfactant at all and suggest a possible synergy with two. Furthermore, because of the easier solubility of the SLS, as compared

TABLE 2

| Example | Metal citrates (ppm) in .4% citric acid | Surfactant* (wt %) | Turbidity (NTU) Time zero | T 1 hour | T 18 hours | T 24 hours | T 96 Hrs |
|---|---|---|---|---|---|---|---|
| 22 | Copper 5 ppm | | 103 | 114 | 410 | 463 | 588 |
| 23 | Zinc 5 ppm | | 103 | 118 | 475 | 488 | 589 |
| 24 | Silver 5 ppm | | 155 | 168 | 181 | 190 | 670 |

TABLE 2-continued

| | | | Turbidity (NTU) | | | | |
|---|---|---|---|---|---|---|---|
| Example | Metal citrates (ppm) in .4% citric acid | Surfactant* (wt %) | Time zero | T 1 hour | T 18 hours | T 24 hours | T 96 Hrs |
| 25 | Copper 5 ppm | .005 NaLS | 145 | 146 | 157 | 160 | 149 |
| 26 | Copper 5 ppm | .005 SLS | 119 | 128 | 252 | 326 | 502 |
| 27 | Copper 5 ppm | .005 NaLS:.005 SLS | 145 | 144 | 156 | 154 | 157 |
| 28 | Zinc 5 ppm | .005 NaLS | 148 | 156 | 157 | 157 | 157 |
| 29 | Zinc 5 ppm | .005 SLS | 126 | 134 | 217 | 234 | 539 |
| 30 | Zinc 5 ppm | .005 NaLS:.005 SLS | 155 | 155 | 157 | 157 | 158 |
| 31 | Silver 5 ppm | .005 NaLS | 170 | 170 | 184 | 184 | 180 |
| 32 | Silver 5 ppm | .005 SLS | 177 | 177 | 193 | 196 | 196 |
| 33 | Silver 5 ppm | .005 NaLS:.005 SLS | 193 | 190 | 198 | 199 | 199 |
| 34 | Copper 2.5 ppm:Zinc 2.5 ppm | | 99 | 109 | 498 | 510 | 614 |
| 35 | Copper 2.5 ppm:Silver 2.5 ppm | | 128 | 152 | 424 | 530 | 727 |
| 36 | Zinc 2.5 ppm:Silver 2.5 ppm | | 128 | 151 | 541 | 621 | 720 |
| 37 | Control 1 (no biocide) | | 91 | 114 | 560 | 580 | 754 |
| 38 | Control 2 (no biocide) | | 91 | 114 | 563 | 584 | 726 |
| 39 | Copper 2.5 ppm:Zinc 2.5 ppm | .005 NaLS:.005 SLS | 192 | 180 | 193 | 193 | 193 |
| 40 | Copper 2.5 ppm:Silver 2.5 ppm | .005 NaLS:.005 SLS | 181 | 204 | 205 | 206 | 206 |
| 41 | Zinc 2.5 ppm:Silver 2.5 ppm | .005 NaLS:.005 SLS | 194 | 193 | 212 | 212 | 212 |
| 42 | Copper 2.5 ppm:Silver 2.5 ppm:Zinc 2.5 ppm | .005 NaLS:.005 SLS | 193 | 193 | 199 | 200 | 205 |

*NaLS - sodium lauroyl sarcosinate, SLS - sodium lauryl sulfate

TABLE 2A

| | | | Change in Turbidity from T0 (delta NTU) | | | |
|---|---|---|---|---|---|---|
| Example | Metal citrates (ppm) in .4% citric acid | Surfactant* (wt %) | T 1 hour | T 18 hours | T 24 hours | T 96 Hrs |
| 22 | Copper 5 ppm | | 11 | 307 | 360 | 485 |
| 23 | Zinc 5 ppm | | 15 | 372 | 385 | 486 |
| 24 | Silver 5 ppm | | 13 | 26 | 35 | 515 |
| 25 | Copper 5 ppm | .005 NaLS | 1 | 12 | 15 | 4 |
| 26 | Copper 5 ppm | .005 SLS | 9 | 133 | 207 | 383 |
| 27 | Copper 5 ppm | .005 NaLS:.005 SLS | −1 | 11 | 9 | 12 |
| 28 | Zinc 5 ppm | .005 NaLS | 8 | 9 | 9 | 9 |
| 29 | Zinc 5 ppm | .005 SLS | 8 | 91 | 108 | 413 |
| 30 | Zinc 5 ppm | .005 NaLS:.005 SLS | 0 | 2 | 2 | 3 |
| 31 | Silver 5 ppm | .005 NaLS | 0 | 14 | 14 | 10 |
| 32 | Silver 5 ppm | .005 SLS | 0 | 16 | 19 | 19 |
| 33 | Silver 5 ppm | .005 NaLS:.005 SLS | −3 | 5 | 6 | 6 |
| 34 | Copper 2.5 ppm:Zinc 2.5 ppm | | 10 | 399 | 411 | 515 |
| 35 | Copper 2.5 ppm:Silver 2.5 ppm | | 24 | 296 | 402 | 599 |
| 36 | Zinc 2.5 ppm:Silver 2.5 ppm | | 23 | 413 | 493 | 592 |
| 37 | Control 1 (no biocide) | | 23 | 469 | 489 | 663 |
| 38 | Control 2 (no biocide) | | 23 | 472 | 493 | 635 |
| 39 | Copper 2.5 ppm:Zinc 2.5 ppm | .005 NaLS:.005 SLS | −12 | 1 | 1 | 1 |
| 40 | Copper 2.5 ppm:Silver 2.5 ppm | .005 NaLS:.005 SLS | 23 | 24 | 25 | 25 |
| 41 | Zinc 2.5 ppm:Silver 2.5 ppm | .005 NaLS:.005 SLS | −1 | 18 | 18 | 18 |
| 42 | Copper 2.5 ppm:Silver 2.5 ppm:Zinc 2.5 ppm | .005 NaLS:.005 SLS | 0 | 6 | 7 | 12 | to the sodium lauroyl sarcosinate (NaLS), the presence of the SLS helps improve and/or enhance the solubility of the NaLS under acid conditions.

Examples 43-57

Low Concentration Evaluation

A series of experiments were conducted again to evaluate the performance of various combinations of the components of the bioactive compositions of the present invention, this time focusing on the impact of the low concentrations of the components and their combinations. In this set of experiments, 1 ml aqueous solutions of the bioactive/citric acid components were added to the 20 ml vials. The specific formulations evaluated and the yeast growth results are presented in Tables 3 and 3A.

As seen in Tables 3 and 3A, once again the combination of bioactive metal ions, citric acid and anionic surfactant demonstrated a marked inhibition in yeast growth as compared to the individual components, even at the low concentrations of excess acid and surfactant. Though, once again, the surfactants appeared to have a marginal inhibitory effect, as compared to the controls, on their own, the inhibition was negligible as compared to that of the systems according to the present invention.

Examples 58-71

Ion-Exchange Metal Ion Source

A metal citrate solution was prepared by adding approximately 4 grams of citric acid to about 8 grams of water and mixed until fully dissolved. Thereafter, 0.1 grams each of two ion-exchange type antimicrobial agents, AgION AC10D and AgION AK10D antimicrobial agents from AgION Technologies of Wakefield, Mass., USA, were added to the concentrated citric acid solution with agitation until the antimicrobial agents fully dissolved. Approximately 92 grams of water was then added to provide a 4% citric acid solution having dissolved therein 0.1 wt % AC10D and 0.1 wt % AK10D.

AgION AK10D contains about 5.0% by weight silver and about 13% by weight zinc and AgION AC10D contains about 6.0% by weight copper and about 3.5% by weight silver. Various quantities of the so formed citric acid solution were then added to test vials so as to provide a silver content in the test vials of approximately 1.25 ppm, 2.5 ppm, 5.0 ppm and 10 ppm. Additionally, different surfactant and surfactant combinations were added to certain vials to demonstrate the effect of different metal and acid contents on bioefficacy with and

TABLE 3

| | | | | Turbidity (NTU) | | | | |
|---|---|---|---|---|---|---|---|---|
| Example | Bioactive Metal* | Citric Acid (wt %) | Surfactant** (wt %) | OD(To) | OD (T1 hr) | OD (T18) | OD (T24) | OD (T48) |
| 43 | | | 0.01 NaLS | 43 | 45 | 550 | 613 | 521 |
| 44 | | | 0.02 NaLS | 43 | 40 | 460 | 524 | 624 |
| 45 | | | 0.01 SLS | 43 | 47 | 675 | 728 | 758 |
| 46 | | | 0.02 SLS | 37 | 42 | 495 | 610 | 605 |
| 47 | | | 0.01 NaLS/0.01 SLS | 40 | 41 | 370 | 466 | 580 |
| 48 | | | 0.005 NaLS/0.005 SLS | 43 | 47 | 630 | 696 | 726 |
| 49 | | 0.05 | | 42 | 46 | 835 | 920 | 878 |
| 50 | | 0.1 | | 38 | 44 | 780 | 864 | 852 |
| 51 | MI1 | 0.2 | | 50 | 62 | 809 | 891 | 915 |
| 52 | MI1 | 0.2 | 0.01 NaLS | 64 | 63 | 67 | 68 | 69 |
| 53 | MI1 | 0.2 | 0.01 SLS | 61 | 65 | 300 | 569 | 1039 |
| 54 | MI1 | 0.2 | 0.005 NaLS/0.005 SLS | 60 | 63 | 62 | 63 | 73 |
| 55 | MI1 | 0.2 | 0.01 NaLS/0.01 SLS | 85 | 76 | 76 | 79 | 79 |
| 56 | Control 1 | | | 43 | 51 | 960 | 997 | 939 |
| 57 | Control 2 | | | 43 | 51 | 890 | 986 | 887 |

*MI1 a 4% citric acid solution containing of 50 ppm each of Ag, Cu and Zn per ml giving (@ 1 ml) ~5 ppm of each in the test vial
**NaLS - sodium lauroyl sarcosinate, SLS - sodium lauryl sulfate

TABLE 3A

| | | | | Change in Turbidity from T0 (delta NTU) | | | |
|---|---|---|---|---|---|---|---|
| Example | Bioactive Metal* | Citric Acid (wt %) | Surfactant** (wt %) | OD (T1 hr) | OD (T18) | OD (T24) | OD (T48) |
| 43 | | | 0.01 NaLS | 2 | 507 | 570 | 478 |
| 44 | | | 0.02 NaLS | −3 | 417 | 481 | 581 |
| 45 | | | 0.01 SLS | 4 | 632 | 685 | 715 |
| 46 | | | 0.02 SLS | 5 | 458 | 573 | 568 |
| 47 | | | 0.01 NaLS/0.01 SLS | 1 | 330 | 426 | 540 |
| 48 | | | 0.005 NaLS/0.005 SLS | 4 | 587 | 653 | 683 |
| 49 | | 0.05 | | 4 | 793 | 878 | 836 |
| 50 | | 0.1 | | 6 | 742 | 826 | 814 |
| 51 | MI1 | 0.2 | | 12 | 759 | 841 | 865 |
| 52 | MI1 | 0.2 | 0.01 NaLS | −1 | 3 | 4 | 5 |
| 53 | MI1 | 0.2 | 0.01 SLS | 4 | 239 | 508 | 978 |
| 54 | MI1 | 0.2 | 0.005 NaLS/0.005 SLS | 3 | 2 | 3 | 13 |
| 55 | MI1 | 0.2 | 0.01 NaLS/0.01 SLS | −9 | −9 | −6 | −6 |
| 56 | Control 1 | | | 8 | 917 | 954 | 896 |
| 57 | Control 2 | | | 8 | 847 | 943 | 844 |

*MI1 a 4% citric acid solution containing of 50 ppm each of Ag, Cu and Zn per ml giving (@ 1 ml) ~5 ppm of each in the test vial
**NaLS—sodium lauroyl sarcosinate, SLS—sodium lauryl sulfate

TABLE 4

| | | | Turbidity (NTU) | | | | | |
|---|---|---|---|---|---|---|---|---|
| Example | Ag Concentration ppm | Surfactant* (wt %) | OD (T zero) | OD (T1 hr) | OD (T18 hr) | OD (T24 hr) | OD (T44 hr) | OD (T120 hr) |
| 58 | 1.25 | | 108 | 128 | 913 | 880 | 954 | 1136 |
| 59 | 2.5 | | 127 | 157 | 865 | 890 | 941 | 1024 |
| 60 | 5 | | 176 | 199 | 229 | 227 | 234 | 721 |
| 61 | 10 | | 168 | 173 | 191 | 191 | 190 | 180 |
| 62 | 1.25 | 0.005 NaLS | 143 | 158 | 240 | 560 | 843 | 708 |
| 63 | 2.5 | 0.005 NaLS | 180 | 179 | 204 | 210 | 729 | 843 |
| 64 | 5 | 0.005 NaLS | 194 | 201 | 222 | 221 | 227 | 227 |
| 65 | 1.25 | 0.005 SLS | 136 | 167 | 953 | 930 | 973 | 1132 |
| 66 | 2.5 | 0.005 SLS | 201 | 212 | 880 | 880 | 967 | 1145 |
| 67 | 5 | 0.005 SLS | 248 | 247 | 272 | 272 | 296 | 297 |
| 68 | 1.25 | .0025 NaLS/.0025 SLS | 166 | 180 | 343 | 730 | 957 | 986 |
| 69 | 2.5 | .0025 NaLS/.0025 SLS | 215 | 217 | 235 | 239 | 759 | 940 |
| 70 | 5 | .0025 NaLS/.0025 SLS | 235 | 235 | 257 | 255 | 259 | 268 |
| 71 | Control | | 101 | 125 | 1050 | 1050 | 1040 | 1183 |

*NaLS—sodium lauroyl sarcosinate, SLS—sodium lauryl sulfate

TABLE 4A

| Example | Ag Concentration ppm | Surfactant* (wt %) | OD (T1 hr) | OD (T18 hr) | OD (T24 hr) | OD (T44 hr) | OD (T120 hr) |
|---|---|---|---|---|---|---|---|
| | | | | Change in Turbidity (delta NTU) | | | |
| 58 | 1.25 | | 20 | 805 | 772 | 846 | 1028 |
| 59 | 2.5 | | 30 | 738 | 763 | 814 | 897 |
| 60 | 5 | | 23 | 53 | 51 | 58 | 545 |
| 61 | 10 | | 5 | 23 | 23 | 22 | 12 |
| 62 | 1.25 | 0.005 NaLS | 15 | 97 | 417 | 700 | 565 |
| 63 | 2.5 | 0.005 NaLS | −1 | 24 | 30 | 549 | 663 |
| 64 | 5 | 0.005 NaLS | 7 | 28 | 27 | 33 | 33 |
| 65 | 1.25 | 0.005 SLS | 31 | 817 | 794 | 837 | 996 |
| 66 | 2.5 | 0.005 SLS | 11 | 679 | 679 | 766 | 944 |
| 67 | 5 | 0.005 SLS | −1 | 24 | 24 | 48 | 49 |
| 68 | 1.25 | .0025 NaLS/.0025 SLS | 14 | 177 | 564 | 791 | 820 |
| 69 | 2.5 | .0025 NaLS/.0025 SLS | 2 | 20 | 24 | 544 | 725 |
| 70 | 5 | .0025 NaLS/.0025 SLS | 0 | 22 | 20 | 24 | 33 |
| 71 | Control | | 24 | 949 | 949 | 939 | 1082 |

*NaLS—sodium lauroyl sarcosinate, SLS—sodium lauryl sulfate without surfactants. The specific formulations evaluated and the yeast growth results are presented in Tables 4 and 4A.

As seen in Tables 4 and 4A, the compositions according to the present invention provided marked inhibition in yeast growth. Although Example 61 containing the higher concentration of metal ions (10 ppm silver, 7 ppm copper and 15.3 ppm zinc), showed good yeast growth inhibition, the higher degree of efficacy comes with the concomitant increase in the release of these metals into the environment. This becomes especially important where the bioactive materials are to be used in or near marine and/or agricultural applications. Thus, while high metal concentrations, especially of silver, will provide better bioefficacy, they also hasten the impact on aquatic environments. On the other hand, as shown in those examples employing the antimicrobial metal containing acid solutions with the anionic surfactant, especially sodium lauroyl sarcosinate, alone or in combination with sodium lauryl sulfate, the same and even better yeast inhibition is realized with less than half, even less than one-quarter, the metal ion concentrations. Furthermore, these results show that by adjusting the level of surfactant, one may reduce the level of metal ion even more while still providing marked inhibition of the fungi.

Also surprising about this example is the finding that citric acid could dissolve the antimicrobial zeolite particles. This finding presents another means by which the inventive compositions may be made as well as a number of alternative applications for such materials not otherwise possible with the zeolites in their solid form.

Examples 72-79

Metal Concentration

For this study a concentrated bioactive system (MI2) was prepared comprising a 16% aqueous citric acid solution having dissolved therein silver citrate, copper citrate and zinc citrate, each added in an amount to provide 200 ppm of each metal, together with 0.25% sodium Lauroyl sarcosinate and 0.32% sodium lauryl sulfate. Various amounts of this system were added to the test vials to further assess the impact of metal concentration yeast inhibition. A further example was prepared further including a non-ionic surfactant, Tween 20 (polyoxyethylene (20) sorbitan monolaurate), an emulsifier to assess its impact on performance. The specific formulations evaluated and the results are presented in Tables 5 and 5A.

As seen in Tables 5 and 5A, the high concentrations of metals dramatically inhibited, if not stopped altogether, yeast growth. The solutions of Examples 76, 77 and 78 containing ultra-high metal content appeared to destroy the yeast cells, showing what appeared to be a rapid denaturation of the yeast on addition of the bioactive material to the text vials. It is likely that the initial high turbidity reflected both that arising from the addition of the bioactive materials themselves as well as the destruction of the yeast cells.

TABLE 5

| Example | MI2* added (ml) | Concentration of each metal (ppm) | Turbidity (NTU) | | | | | |
|---|---|---|---|---|---|---|---|---|
| | | | T0 | T18 | T22 | T24 | T64 | T82 |
| 72 | 0 | 0 | 63 | 920 | 980 | 964 | 1020 | 1050 |
| 73 | 0.1 | 1 | 81 | 608 | 722 | 820 | 1077 | 1062 |
| 74 | 0.25 | 2.5 | 111 | 126 | 142 | 160 | 752 | 810 |
| 75 | 0.5 | 5 | 145 | 198 | 208 | 208 | 205 | 203 |
| 76 | 1.0 | 10 | 483 | 410 | 395 | 369 | 320 | 300 |
| 77 | 2.0 | 20 | 1295 | 820 | 714 | 660 | 399 | 264 |
| 78 | 3.0 | 30 | 1435 | 766 | 620 | 555 | 340 | 340 |
| 79 | 0.5+ | 5 | 141 | 249 | 405 | 600 | 1116 | 1129 |

*MI2 a 16% citric acid solution containing of 200 ppm each of Ag, Cu and Zn per ml
+this formulation also contained 0.1 wt % Tween 20 a non-ionic surfactant

TABLE 5A

| Example | MI2* added (ml) | Concentration of each metal (ppm) | Change in Turbidity (delta NTU) | | | | |
|---|---|---|---|---|---|---|---|
| | | | T18 − T0 | T22 − T0 | T24 − T0 | T64 − T0 | T82 − T0 |
| 72 | 0 | 0 | 857 | 917 | 901 | 957 | 987 |
| 73 | 0.1. | 1 | 527 | 641 | 739 | 996 | 981 |
| 74 | 0.25 | 2.5 | 15 | 31 | 49 | 641 | 699 |

TABLE 5A-continued

| Example | MI2* added (ml) | Concentration of each metal (ppm) | Change in Turbidity (delta NTU) | | | | |
|---|---|---|---|---|---|---|---|
| | | | T18 – T0 | T22 – T0 | T24 – T0 | T64 – T0 | T82 – T0 |
| 75 | 0.5 | 5 | 53 | 63 | 63 | 60 | 58 |
| 76 | 1.0 | 10 | −73 | −88 | −114 | −163 | −183 |
| 77 | 2.0 | 20 | −475 | −581 | −635 | −896 | −1031 |
| 78 | 3.0 | 30 | −669 | −815 | −880 | −1095 | −1095 |
| 79 | 0.5⁺ | 5 | 108 | 264 | 459 | 975 | 988 |

*MI2 a 16% citric acid solution containing of 200 ppm each of Ag, Cu and Zn per ml
⁺this formulation also contained 0.1 wt % Tween 20 a non-ionic surfactant Regardless, the results show that marked inhibition is also attained at much lower concentrations of the metal in the presence of the excess acid and surfactant. Indeed, just 15 ppm metals (5 ppm of each) provide excellent inhibition through 82 hours and beyond.

Finally, the addition of Tween 20 surfactant appeared to be antagonistic to the action of the bioactive systems of the present invention resulting in a reduction in the level of yeast inhibition. Still, this composition (Example 79) manifested moderate yeast inhibition through 24 hours. Depending upon the specific end-use application contemplated, it is evident that routine preliminary evaluations should be conducted before formulating with various additives to ascertain their impact on the inventive systems of the present invention.

Examples 80-95

Bioactives Synergy

A series of experiments were conducted in which possible synergies were evaluated between the inventive compositions and other bioactive materials as well as between such other bioactive materials including a fungicide, an antimicrobial agent and a disinfectant. The inventive bioactive system employed in this set of experiments (MI3) was a 4% aqueous citric acid solution containing 50 ppm silver, 50 ppm copper and 50 ppm zinc.

The fungicide evaluated was Mancozeb Flowable with Zinc from Bonide Products, Inc. of Oniskany, N.Y., USA, a commercial formulated fungicide containing 37% by wt mancozeb. Although the specific formulation of the Mancozeb product is proprietary, as a commercial formulation it would also contain certain surfactants for enabling its application to plants for efficacy. Mancozeb is an insoluble, dispersible powder that increases the turbidity of the liquids to which it is added. Nevertheless, in a separate evaluation, not reproduced here, it was found that Mancozeb was able to control or inhibit yeast growth at a concentration of about $1.23 \times 10^{-3}$. The label indicates its use rate at $2.6 \times 10^{-3}$.

The antimicrobial active evaluated was AgION AC10D, an antimicrobial zeolite additive available from AgION Technologies, Inc., of Wakefield, Mass., USA, which, as noted above, contains 6.0 wt % copper and 3.5 wt % silver. In a separate dilution evaluation, not reproduced here, it was found that an aqueous suspension of AC10D showed some yeast control or inhibition at a concentration of about $6.25 \times 10^{-4}$.

Finally, the disinfectant evaluated was AgION SilverClene 24, a disinfectant material based on an aqueous solution of electrolytically generated silver citrate (~30 ppm silver), also distributed by AgION Technologies, Inc. Although proprietary, this product and its manufacture is believed to be disclosed in Arata—U.S. Pat. No. 6,583,176, which is incorporated herein by reference in its entirety.

The aforementioned materials as well as various combinations thereof were evaluated to assess their efficacy in stopping or inhibiting the growth of yeast. The specific formulations tested and the yeast inhibition results attained therewith are presented in Tables 6 and 6A.

TABLE 6

| Example | Amt MI3 (ml) | Mancozeb (wt %) | AgION AC10D (wt %) | SilverClene 24 (ml) | Surfactant (wt %) | Turbidity (NTU) | | | | pH |
|---|---|---|---|---|---|---|---|---|---|---|
| | | | | | | OD T zero | T (1 hour) | T (18 hour) | T (24 Hour) | |
| 80 | | 9.40E−05 | | | | 262 | 293 | 1023 | 1030 | 3.07 |
| 81 | 1 | 9.40E−05 | | | | 276 | 276 | 309 | 522 | 2.91 |
| 82 | 2 | 9.40E−05 | | | | 301 | 301 | 308 | 312 | 2.55 |
| 83 | 2 | 1.88E−04 | | | 0.05 NaLS/0.05 SLS | 350 | 362 | 362 | 362 | |
| 84 | 2 | 3.75E−04 | | | | 656 | 640 | 1001 | 1170 | 2.4 |
| 85 | 1 | 9.40E−05 | | | 0.05 SLS | 331 | 321 | 328 | 330 | 2.48 |
| 86 | to pH 6 | 3.75E−04 | | | 0.05 NaLS/0.05 SLS | 609 | 605 | 825 | 968 | 4.91 |
| 87 | | 1.88E−04 | 7.81E−05 | | 0.05 NaLS | 410 | 385 | 443 | 511 | |
| 88 | 2 | 1.88E−04 | 7.81E−05 | | 0.05 NaLS/0.05 SLS | 521 | 435 | 435 | 440 | 2.68 |
| 89 | | 9.40E−05 | | 1 | | 258 | 276 | 970 | 962 | 2.67 |
| 90 | | 1.88E−04 | | 2 | | 365 | 364 | 782 | 1048 | |
| 91 | | | 3.90E−05 | | | 128 | 151 | 862 | 800 | 3.23 |
| 92 | 2 | | 3.90E−05 | | 0.05 SLS | 154 | 156 | 172 | 175 | 2.54 |
| 93 | 2 | | 1.56E−04 | | 0.05 NaLS/0.05 SLS | 190 | 143 | 148 | 156 | 2.66 |
| 94 | 2 | | | | 0.05 NaLS/0.05 SLS | 157 | 67 | 189 | 195 | 2.51 |
| 95 | Control | | | | | 73 | 98 | 898 | 856 | 3.25 |

TABLE 6A

| Example | Amt MI3 (ml) | Mancozeb (wt %) | AgION AC10D (wt %) | SilverClene 24 (ml) | Surfactant (wt %) | Change in Turbidity (delta NTU) | | | | |
|---|---|---|---|---|---|---|---|---|---|---|
| | | | | | | 1 hour | 18 hour | 1 – 18 hour | 24 hour | 1 – 24 hour |
| 80 | | 9.40E−05 | | | | 31 | 761 | 730 | 768 | 737 |
| 81 | 1 | 9.40E−05 | | | | 0 | 33 | 33 | 246 | 246 |
| 82 | 2 | 9.40E−05 | | | | 0 | 7 | 7 | 11 | 11 |
| 83 | 2 | 1.88E−04 | | | 0.05 NaLS/0.05 SLS | 12 | 12 | 0 | 12 | 0 |
| 84 | 2 | 3.75E−04 | | | | −16 | 345 | 361 | 514 | 530 |
| 85 | 1 | 9.40E−05 | | | 0.05 SLS | −10 | −3 | 7 | −1 | 9 |
| 86 | to pH 6 | 3.75E−04 | | | 0.05 NaLS/0.05 SLS | −4 | 216 | 220 | 359 | 363 |
| 87 | | 1.88E−04 | 7.81E−05 | | 0.05 NaLS | −25 | 33 | 58 | 101 | 126 |
| 88 | 2 | 1.88E−04 | 7.81E−05 | | 0.05 NaLS/0.05 SLS | −86 | −86 | 0 | −81 | 5 |
| 89 | | 9.40E−05 | | 1 | | 18 | 712 | 694 | 704 | 686 |
| 90 | | 1.88E−04 | | 2 | | −1 | 417 | 416 | 683 | 682 |
| 91 | | | 3.90E−05 | | | 23 | 734 | 711 | 672 | 649 |
| 92 | 2 | | 3.90E−05 | | 0.05 SLS | 2 | 18 | 16 | 21 | 19 |
| 93 | 2 | | 1.56E−04 | | 0.05 NaLS/0.05 SLS | −47 | −42 | 5 | −34 | 13 |
| 94 | 2 | | | | 0.05 NaLS/0.05 SLS | −90 | 32 | 122 | 38 | 128 |
| 95 | Control | | | | | 25 | 825 | 800 | 783 | 758 |

The results presented in Tables 6 and 6A demonstrate a marked synergy between the inventive compositions according the present invention and commercial fungicides and antimicrobial agents. Specifically, for example, a comparison of the results for Examples 80, 81 and 82 demonstrate that combining low amounts of the metal ions, citric acid and fungicide provided excellent antifungal performance. While it is noted that these formulations did not have additional surfactant, the commercial fungicide itself contained surfactants that worked in combination with the metal ions and citric acid to provide the benefits owing to that combination as now claimed. These results show that excellent antifungal activity, as measured by yeast growth inhibition, may be attained with less than 10% of the amount of fungicide needed to inhibit yeast growth by the simple addition of low levels of acid and metal ions. As seen from Examples 91, 92 and 93, a similar synergy is shown for the inventive compositions in combination with a conventional inorganic antimicrobial agent. Here too, less than 10% of that amount of the antimicrobial agent needed when used alone, provided good antimicrobial performance when in combination with low levels of bioactive composition according to the present invention. However, the substitution of the SilverClene 24 for the inventive composition of the present invention, Examples 89 and 90, provided no apparent benefit despite the relatively high silver content.

Finally, in Example 86, ammonia was added to a portion of the M13 solution until the solution reached a pH of 6. 2 ml of this buffered solution was then employed in the experiment. This example indicates the importance of the low pH of the compositions according to the present invention in order to provide desirable performance.

Examples 96-107

Immunox Synergy

A similar study was conducted to assess the synergy between the bioactive compositions according to the present invention and a second fungicide, Immunox, a commercial fungicide containing 1.55% myclobutanil, available from Spectrum Brands Division of United Industries of Madison, Wis., USA. As a commercial formulation, this too is expected to have some surfactants content. The bioactive composition employed in this experiment was the concentrated bioactive system (MI2) produced in Examples 72-79 above. The specific dilutions of each and the results attained thereby are presented in Table 7.

TABLE 7

| | Dilution Ratio | | | T1.5 | | | Delta |
|---|---|---|---|---|---|---|---|
| Example | Immunox | MI2 | T zero | OD | T18 | T68 OD | 68 |
| 96 | | 1:80 | 150 | 152 | | 832 | 682 |
| 97 | | 1:200 | 106 | 112 | | 980 | 874 |
| 98 | 1:64 | | 97 | 107 | 1043 | | |
| 99 | 1:128 | | 111 | 119 | 1126 | | |
| 100 | 1:256 | | 84 | 131 | | 1170 | 1086 |
| 101 | 1:512 | | 81 | 140 | | 1240 | 1159 |
| 102 | 1:256 | 1:80 | 138 | 141 | | 268 | 130 |
| 103 | 1:256 | 1:200 | 102 | 114 | | 1037 | 935 |
| 104 | 1:512 | 1:80 | 138 | 140 | | 292 | 154 |
| 105 | 1:512 | 1:200 | 97 | 110 | | 1031 | 934 |
| 106 | Control 1 | | 86 | 175 | | 754 | 668 |
| 107 | Control 2 | | 87 | 176 | | 1180 | 1093 |

As indicated in Table 7, none of the test vials containing the low levels of each of the bioactive compositions or the Immunox dilution provided antifungal activity through the full 96 hour period tested. Furthermore, neither the 1:128 dilution (Example 99) nor the 1:64 dilution (Example 98) of Immunox provided any measure of efficacy, even in the shorter test period of 18 hours, despite the fact that the manufacturer generally recommends a dilution of 1:64. Similarly, Examples 103 and 105 having a 1:200 dilution of the bioactive composition (~1 ppm of each metal, 0.08% citric acid, 0.00125 NaLS and 0.0016 SLS) in combination with the two dilutions of the Immunox failed to demonstrate bioefficacy whereas combinations of both dilutions of the Immunox with a somewhat higher level, 1:80 dilution, of the bioactive composition (~2.5 ppm of each metal, 0.2% citric acid, 0.003 NaLS and 0.004 SLS) demonstrated bioefficacy. This demonstrates a synergy between the two compositions as the 1:80 dilution by itself failed to show bioefficacy over the full period tested.

Examples 108-126

Metal Sources

A series of experiments were conducted using different metal salts as the metal ion sources. Here, sufficient amounts of silver nitrate, copper sulfate and zinc oxide were added to a 5% aqueous citric acid solution to provide 31.75 ppm silver, 12.5 ppm copper and 40.17 ppm zinc. Different quantities of this stock concentrate solution (MI4) were added to the test vials to assess efficacy. The specific formulations, including the resultant ppm of each metal in the text vial, as well as the results thereof in inhibiting yeast growth were as presented in Tables 8 and 8A.

The results shown in Tables 8 and 8A demonstrate that the selection of the metal ion source is not critical so long as it is readily soluble and is soluble to the extent needed to provide the desired level of metal ion concentration in the solution. Furthermore, the results demonstrate the bioefficacy even at extremely low metal and acid contents. Although, the efficacy is relatively short lived at the lower concentrations, long-term bioefficacy is found with only minor adjustments in the relative concentration of the necessary components. Furthermore, depending upon the ultimate end-use application, such short term antifungal efficacy may be sufficient; thus, enabling one to minimize any environmental contamination from the general application of these materials.

The results also suggest that sodium lauryl sulfate may be ineffective on its own in promoting the bioefficacy of the bioactive compositions of the present invention. Nevertheless, its presence may be desirable where the efficacious surfactant is not readily soluble in the aqueous system. On the other hand, its presence or the presence of like surfactants may not be important where the intent is to produce non-aqueous systems. For example, systems to be applied as an emulsion in water or as an oil that will spread on an aqueous medium to which it is applied, e.g., a rice paddy, may look to surfactants that are less hydrophilic and more lipophilic.

Examples 127-143

Lactic Acid

A series of experiments was conducted similar to the previous with the exception that lactic acid was substituted for citric acid. Hence, the bioactive composition (MI5) comprised sufficient amounts of silver nitrate, copper sulfate and zinc oxide dissolved in a 5% aqueous lactic acid solution to provide 31.75 ppm silver, 12.5 ppm copper and 40.17 ppm zinc. The specific formulations tested and the results attained therewith were as presented in Tables 9 and 9A.

TABLE 8

| Example | Volume MI4 added | Metals Concentration | | | Surfactant (w/w)% | | Turbidity (NTU) | | | | | | |
|---|---|---|---|---|---|---|---|---|---|---|---|---|---|
| | | ppm Ag | ppm Cu | ppm Zn | NaLS | SDS | T zero | T2 | T18 | T26 | T44 | T48 | T68 |
| 108 | 0.5 | 0.79 | 0.31 | 1.00 | | | 81 | 129 | 950 | 1046 | 1046 | 1046 | 1054 |
| 109 | 1 | 1.59 | 0.63 | 2.01 | | | 85 | 136 | 950 | 997 | 1055 | 990 | 1023 |
| 110 | 2 | 3.18 | 1.25 | 4.02 | | | 112 | 158 | 916 | 930 | 960 | 930 | 970 |
| 111 | 3 | 4.76 | 1.88 | 6.03 | | | 126 | 158 | 760 | 799 | 810 | 830 | 844 |
| 112 | 0.5 | 0.79 | 0.31 | 1.00 | 0.005 | | 140 | 143 | 179 | 307 | 919 | 936 | 980 |
| 113 | 1 | 1.59 | 0.63 | 2.01 | 0.005 | | 140 | 137 | 143 | 152 | 279 | 306 | 468 |
| 114 | 2 | 3.18 | 1.25 | 4.02 | 0.005 | | 180 | 174 | 174 | 177 | 244 | 252 | 282 |
| 115 | 3 | 4.76 | 1.88 | 6.03 | 0.005 | | 187 | 185 | 184 | 184 | 184 | 184 | 272 |
| 116 | 0.5 | 0.79 | 0.31 | 1.00 | | 0.005 | 83 | 132 | 948 | 1054 | 1066 | 1078 | 1097 |
| 117 | 1 | 1.59 | 0.63 | 2.01 | | 0.005 | 97 | 136 | 911 | 1003 | 1100 | 1060 | 1075 |
| 118 | 2 | 3.18 | 1.25 | 4.02 | | 0.005 | 116 | 147 | 746 | 907 | 970 | 1001 | 1006 |
| 119 | 3 | 4.76 | 1.88 | 6.03 | | 0.005 | 124 | 156 | 504 | 701 | 840 | 868 | 916 |
| 120 | 0.5 | 0.79 | 0.31 | 1.00 | 0.0025 | 0.0025 | 140 | 140 | 250 | 640 | 1065 | 1088 | 1133 |
| 121 | 1 | 1.59 | 0.63 | 2.01 | 0.0025 | 0.0025 | 149 | 149 | 160 | 256 | 930 | 901 | 1014 |
| 122 | 2 | 3.18 | 1.25 | 4.02 | 0.0025 | 0.0025 | 164 | 177 | 174 | 174 | 291 | 459 | 804 |
| 123 | 3 | 4.76 | 1.88 | 6.03 | 0.0025 | 0.0025 | 176 | 179 | 177 | 181 | 320 | 445 | 736 |
| 124 | 2 | 3.18 | 1.25 | 4.02 | 0.01 | | 162 | 162 | 162 | 163 | 163 | 164 | 164 |
| 125 | 0.86 | 1.37 | 0.54 | 1.73 | 0.01 | | 150 | 140 | 140 | 140 | 186 | 208 | 254 |
| 126 | | | | | | | 78 | 113 | 877 | 866 | 878 | 865 | 898 |

TABLE 8A

| Example | Volume MI4 added | Metals Concentration | | | Surfactant (w/w)% | | Change in Turbidity (delta NTU) | | | | | |
|---|---|---|---|---|---|---|---|---|---|---|---|---|
| | | ppm Ag | ppm Cu | ppm Zn | NaLS | SDS | Delta T2 − T0 | D T18 − T0 | D T26 − T0 | D T44 − T0 | D T48 − T0 | D T68 − T0 |
| 108 | 0.5 | 0.79 | 0.31 | 1.00 | | | 48 | 869 | 965 | 965 | 965 | 973 |
| 109 | 1 | 1.59 | 0.63 | 2.01 | | | 51 | 865 | 912 | 970 | 905 | 938 |
| 110 | 2 | 3.18 | 1.25 | 4.02 | | | 48 | 804 | 818 | 848 | 818 | 858 |
| 111 | 3 | 4.76 | 1.88 | 6.03 | | | 32 | 624 | 673 | 684 | 704 | 718 |
| 112 | 0.5 | 0.79 | 0.31 | 1.00 | 0.005 | | 3 | 39 | 167 | 779 | 796 | 840 |
| 113 | 1 | 1.59 | 0.63 | 2.01 | 0.005 | | −3 | 3 | 12 | 139 | 166 | 328 |
| 114 | 2 | 3.18 | 1.25 | 4.02 | 0.005 | | −8 | −6 | −3 | 64 | 72 | 102 |
| 115 | 3 | 4.76 | 1.88 | 6.03 | 0.005 | | −2 | −3 | −3 | −3 | −3 | 85 |
| 116 | 0.5 | 0.79 | 0.31 | 1.00 | | 0.005 | 49 | 865 | 971 | 983 | 995 | 1014 |
| 117 | 1 | 1.59 | 0.63 | 2.01 | | 0.005 | 39 | 814 | 906 | 1003 | 963 | 978 |
| 118 | 2 | 3.18 | 1.25 | 4.02 | | 0.005 | 31 | 630 | 791 | 854 | 885 | 890 |
| 119 | 3 | 4.76 | 1.88 | 6.03 | | 0.005 | 32 | 380 | 577 | 716 | 744 | 792 |
| 120 | 0.5 | 0.79 | 0.31 | 1.00 | 0.0025 | 0.0025 | 0 | 110 | 500 | 925 | 948 | 993 |
| 121 | 1 | 1.59 | 0.63 | 2.01 | 0.0025 | 0.0025 | 0 | 11 | 107 | 781 | 752 | 865 |
| 122 | 2 | 3.18 | 1.25 | 4.02 | 0.0025 | 0.0025 | 13 | 10 | 10 | 127 | 295 | 640 |

TABLE 8A-continued

| | Volume | Metals Concentration | | | Surfactant (w/w)% | | Change in Turbidity (delta NTU) | | | | | |
|---|---|---|---|---|---|---|---|---|---|---|---|---|
| Example | MI4 added | ppm Ag | ppm Cu | ppm Zn | NaLS | SDS | Delta T2 – T0 | D T18 – T0 | D T26 – T0 | D T44 – T0 | D T48 – T0 | D T68 – T0 |
| 123 | 3 | 4.76 | 1.88 | 6.03 | 0.0025 | 0.0025 | 3 | 1 | 5 | 144 | 269 | 560 |
| 124 | 2 | 3.18 | 1.25 | 4.02 | 0.01 | | 0 | 0 | 1 | 1 | 2 | 2 |
| 125 | 0.86 | 1.37 | 0.54 | 1.73 | 0.01 | | −10 | −10 | −10 | 36 | 58 | 104 |
| 126 | | | | | | | 35 | 799 | 788 | 800 | 787 | 820 |

TABLE 9

| | Volume MI5 | Metals Concentration | | | Surfactant (w/w)% | | Turbidity (NTU) | | | | |
|---|---|---|---|---|---|---|---|---|---|---|---|
| Example | added | ppm Ag | ppm Cu | ppm Zn | NaLS | SDS | T zero | T1 | T18 | T24 | T44 |
| 127 | 0.5 | 0.79 | 0.31 | 1.00 | | | 107 | 130 | 1000 | 1111 | 1001 |
| 128 | 1 | 1.59 | 0.63 | 2.01 | | | 109 | 130 | 1006 | 1021 | 1016 |
| 129 | 2 | 3.18 | 1.25 | 4.02 | | | 148 | 154 | 970 | 995 | 1014 |
| 130 | 3 | 4.76 | 1.88 | 6.03 | | | 178 | 202 | 914 | 925 | 990 |
| 131 | 0.5 | 0.79 | 0.31 | 1.00 | 0.005 | | 134 | 170 | 300 | 454 | 923 |
| 132 | 1 | 1.59 | 0.63 | 2.01 | 0.005 | | 153 | 169 | 200 | 227 | 292 |
| 133 | 2 | 3.18 | 1.25 | 4.02 | 0.005 | | 218 | 217 | 207 | 204 | 228 |
| 134 | 3 | 4.76 | 1.88 | 6.03 | 0.005 | | 222 | 223 | 222 | 215 | 227 |
| 135 | 0.5 | 0.79 | 0.31 | 1.00 | | 0.005 | 120 | 145 | 1074 | 1111 | 1079 |
| 136 | 1 | 1.59 | 0.63 | 2.01 | | 0.005 | 140 | 156 | 1050 | 1092 | 1110 |
| 137 | 2 | 3.18 | 1.25 | 4.02 | | 0.005 | 179 | 193 | 945 | 1031 | 1080 |
| 138 | 3 | 4.76 | 1.88 | 6.03 | | 0.005 | 223 | 239 | 690 | 977 | 1180 |
| 139 | 0.5 | 0.79 | 0.31 | 1.00 | 0.0025 | 0.0025 | 143 | 151 | 884 | 968 | 1170 |
| 140 | 1 | 1.59 | 0.63 | 2.01 | 0.0025 | 0.0025 | 175 | 175 | 237 | 330 | 1110 |
| 141 | 2 | 3.18 | 1.25 | 4.02 | 0.0025 | 0.0025 | 210 | 214 | 207 | 223 | 730 |
| 142 | 3 | 4.76 | 1.88 | 6.03 | 0.0025 | 0.0025 | 240 | 240 | 228 | 228 | 475 |
| 143 | control | | | | | | 100 | 139 | 1175 | 1163 | 1170 |

TABLE 9A

| | Volume MI5 | Metals Concentration | | | Surfactant (w/w)% | | Change in Turbidity (delta NTU) | | | |
|---|---|---|---|---|---|---|---|---|---|---|
| Example | added | ppm Ag | ppm Cu | ppm Zn | NaLS | SDS | D T1 – T0 | D T18 – T10 | D T24 – T0 | D T44 – T0 |
| 127 | 0.5 | 0.79 | 0.31 | 1.00 | | | 23 | 893 | 1004 | 894 |
| 128 | 1 | 1.59 | 0.63 | 2.01 | | | 21 | 897 | 912 | 907 |
| 129 | 2 | 3.18 | 1.25 | 4.02 | | | 8 | 822 | 847 | 866 |
| 130 | 3 | 4.76 | 1.88 | 6.03 | | | 24 | 736 | 747 | 812 |
| 131 | 0.5 | 0.79 | 0.31 | 1.00 | 0.005 | | 36 | 166 | 320 | 789 |
| 132 | 1 | 1.59 | 0.63 | 2.01 | 0.005 | | 16 | 47 | 74 | 139 |
| 133 | 2 | 3.18 | 1.25 | 4.02 | 0.005 | | −1 | −11 | −14 | 10 |
| 134 | 3 | 4.76 | 1.88 | 6.03 | 0.005 | | 1 | 0 | −7 | 5 |
| 135 | 0.5 | 0.79 | 0.31 | 1.00 | | 0.005 | 25 | 954 | 991 | 959 |
| 136 | 1 | 1.59 | 0.63 | 2.01 | | 0.005 | 16 | 910 | 952 | 970 |
| 137 | 2 | 3.18 | 1.25 | 4.02 | | 0.005 | 14 | 766 | 852 | 901 |
| 138 | 3 | 4.76 | 1.88 | 6.03 | | 0.005 | 16 | 467 | 754 | 957 |
| 139 | 0.5 | 0.79 | 0.31 | 1.00 | 0.0025 | 0.0025 | 8 | 741 | 825 | 1027 |
| 140 | 1 | 1.59 | 0.63 | 2.01 | 0.0025 | 0.0025 | 0 | 62 | 155 | 935 |
| 141 | 2 | 3.18 | 1.25 | 4.02 | 0.0025 | 0.0025 | 4 | −3 | 13 | 520 |
| 142 | 3 | 4.76 | 1.88 | 6.03 | 0.0025 | 0.0025 | 0 | −12 | −12 | 235 |
| 143 | control | | | | | | 39 | 1075 | 1063 | 1070 |

The results as shown in Tables 9 and 9A, mimic those found in the previous set of experiments indicating that the invention is translatable to acids of similar characteristics.

Examples 144-156

Phosphoric Acid

Two stock solutions were prepared for evaluation wherein the acid employed was phosphoric acid. In the first, silver citrate, copper citrate and zinc citrate were added to a 16% aqueous phosphoric acid solution to provide 200 ppm of each metal. A second stock solution was prepared using silver nitrate, copper sulfate and zinc oxide, again in the 16% phosphoric acid solution to provide 200 ppm of each metal. Both composition further contained 0.32% surfactant, either as an individual surfactant or as a 50:50 mix. The specific formulations and the results of their efficacy in controlling yeast growth were as presented in Tables 10 and 10A.

The results as shown in Tables 10 and 10A suggest that the surfactant may not be critical in those compositions wherein the excess acid is a strong to moderate acid, such as phosphoric acid.

Examples 157-166

Nitric Acid

To further demonstrate the breadth of the bioactive compositions, a relatively strong mineral acid, nitric acid, was employed as the acid component. A stock solution was prepared by combining 78.7 mg silver nitrate, 62.2 mg zinc oxide and 200 mg copper sulfate with 20 ml of purified water and 1.5 g concentrated nitric acid (68%) under constant agitation. Once the solids were dissolved, additional purified water was added to make up a 250 volume. As prepared, this mixture contained approximately 200 ppm of each metal, as calculated. The pH was measured and found to be 1.66. The mixture was then divided into three aliquots of approximately equal volume. One aliquot was set aside and the other two were subjected to pH adjustment with ammonia hydroxide. The amount of ammonia hydroxide was added was that necessary to bring the pH of the first aliquot up to 2.55 and the second aliquot up to 3.63.

Each solution was then evaluated, with and without surfactants, to assess their bioefficacy in inhibiting the growth of yeast. The amount of each of the three aliquots added to the 20 ml vial of the yeast suspension is set forth in

TABLE 10

| Example | Metal source | Metal (ppm) | Surfactants (w/w) | Turbidity (NTU) | | | | | | | |
|---|---|---|---|---|---|---|---|---|---|---|---|
| | | | | T zero | T1 hour | T18 | T24 | T42 | T48 | T72 | T96 |
| 144 | Citrate salts* | 2.5 | | 123 | 134 | 300 | 400 | 1046 | 1094 | 1146 | 1106 |
| 145 | Citrate salts* | 5 | | 199 | 180 | 166 | 166 | 160 | 163 | 162 | 154 |
| 146 | Citrate salts* | 10 | | 211 | 193 | 176 | 176 | 172 | 177 | 172 | 169 |
| 147 | AgNO3, CuSO4, ZnO | 2.5 | | 168 | 166 | 179 | 179 | 172 | 174 | 778 | 1162 |
| 148 | AgNO3, CuSO4, ZnO | 5 | | 209 | 193 | 180 | 180 | 175 | 174 | 170 | 168 |
| 149 | AgNO3, CuSO4, ZnO | 10 | | 228 | 219 | 197 | 197 | 196 | 204 | 199 | 194 |
| 150 | Citrate salts* | 5 | 0.05 SLS | 226 | 218 | 200 | 200 | 193 | 203 | 192 | 186 |
| 151 | Citrate salts* | 5 | 0.05 NaLS | 258 | 254 | 216 | 216 | 200 | 205 | 197 | 185 |
| 152 | Citrate salts* | 5 | 0.05 SLS/0.05 NaLS | 253 | 237 | 200 | 200 | 204 | 208 | 201 | 188 |
| 153 | AgNO3, CuSO4, ZnO | 5 | 0.05 SLS | 285 | 263 | 229 | 229 | 223 | 229 | 214 | 206 |
| 154 | AgNO3, CuSO4, ZnO | 5 | 0.05 NaLS | 280 | 273 | 226 | 222 | 216 | 213 | 208 | 184 |
| 155 | AgNO3, CuSO4, ZnO | 5 | 0.05 SLS/0.05 NaLS | 283 | 272 | 250 | 247 | 232 | 238 | 232 | 215 |
| 156 | Control | | | 52 | 53 | 437 | 599 | 938 | 913 | 877 | 886 |

*Ag citrate, Cu citrate and Zn citrate, each at level designated

TABLE 10A

| Example | Metal source | Metal (ppm) | Surfactants (w/w) | Change in Turbidity (delta NTU) | | | | | | |
|---|---|---|---|---|---|---|---|---|---|---|
| | | | | T1 – T0 | T18 – T1 | T24 – T1 | T42 – T1 | T48 – T1 | T72 – T1 | T96 – T1 |
| 144 | Citrate salts* | 2.5 | | 11 | 166 | 266 | 912 | 960 | 1012 | 972 |
| 145 | Citrate salts* | 5 | | −19 | −14 | −14 | −20 | −17 | −18 | −26 |
| 146 | Citrate salts* | 10 | | −18 | −17 | −17 | −21 | −16 | −21 | −24 |
| 147 | AgNO3, CuSO4, ZnO | 2.5 | | −2 | 13 | 13 | 6 | 8 | 612 | 996 |
| 148 | AgNO3, CuSO4, ZnO | 5 | | −16 | −13 | −13 | −18 | −19 | −23 | −25 |
| 149 | AgNO3, CuSO4, ZnO | 10 | | −9 | −22 | −22 | −23 | −15 | −20 | −25 |
| 150 | Citrate salts* | 5 | 0.05 SLS | −8 | −18 | −18 | −25 | −15 | −26 | −32 |
| 151 | Citrate salts* | 5 | 0.05 NaLS | −4 | −38 | −38 | −54 | −49 | −57 | −69 |
| 152 | Citrate salts* | 5 | 0.05 SLS/0.05 NaLS | −16 | −37 | −37 | −33 | −29 | −36 | −49 |
| 153 | AgNO3, CuSO4, ZnO | 5 | 0.05 SLS | −22 | −34 | −34 | −40 | −34 | −49 | −57 |
| 154 | AgNO3, CuSO4, ZnO | 5 | 0.05 NaLS | −7 | −47 | −51 | −57 | −60 | −65 | −89 |
| 155 | AgNO3, CuSO4, ZnO | 5 | 0.05 SLS/0.05 NaLS | −11 | −22 | −25 | −40 | −34 | −40 | −57 |
| 156 | Control | | | 1 | 384 | 546 | 885 | 860 | 824 | 833 |

Table 11 together with the amount of surfactant added, where indicated. The surfactant employed was a 50:50 mix of sodium lauryl sulfate and sodium lauroyl sarcosinate. The specific formulations tested and the results thereof are presented in Table 11. As can be seen from Table 11, the combination of metal and acid did not provide any inhibition at the levels tested. However, when the surfactant was added, bioefficacy was manifested even at the lower metal/acid concentration.

TABLE 11

Nitric Acid

| Example | Vol. MI6 Added | Metals (ppm) | Surfactant (w/w) % | pH | T0 | T18 | T18 − T0 | T42 | T42 − T0 |
|---|---|---|---|---|---|---|---|---|---|
| 157 | 0.5 | 5 | | 1.66 | 69 | 1243 | 1174 | 1133 | 1064 |
| 158 | 0.5 | 5 | | 2.55 | 67 | 1245 | 1178 | 1133 | 1066 |
| 159 | 0.5 | 5 | | 3.63 | 69 | 1243 | 1174 | 1150 | 1081 |
| 160 | 1 | 10 | | 1.66 | 65 | 976 | 911 | 1162 | 1097 |
| 161 | 1 | 10 | | 2.55 | 66 | 1012 | 946 | 1186 | 1120 |
| 162 | 1 | 10 | | 3.63 | 67 | 1036 | 969 | 1166 | 1099 |
| 163 | 0.5 | 5 | 0.05 | 1.66 | 61 | 55 | −6 | 58 | −3 |
| 164 | 0.5 | 5 | 0.05 | 2.55 | 62 | 53 | −9 | 55 | −7 |
| 165 | 0.5 | 5 | 0.05 | 3.63 | 60 | 57 | −3 | 52 | −8 |
| 166 | 0 | | | | 67 | 1255 | 1188 | 1212 | 1145 |

Examples 167-222

Surfactant Evaluation

A series of experiments were conducted to screen various surfactants for efficacy in accordance with the present invention. The surfactants were evaluated as a neat additive (0 ppm metals) or in combination with either 1 ml or 2 ml of a 4% citric acid solution containing 50 ppm each of copper, silver and zinc. With the addition of 1 ml of the citric acid solution, the test vial of the yeast suspension will have about 0.2% citric acid and about 2.5 ppm of each metal. With the addition of 2 ml of the citric acid solution, the acid is approximately 0.4% and the metals are each present at about 5 ppm in the test vials. Each surfactant was evaluated at a concentration of approximately 0.05 wt %. Controls were also evaluated with and without the metals.

The specific surfactants evaluated as well as the formulations of each test composition together with the results thereof are set forth in Table 12. As

TABLE 12

| Example | Surfactants | Surfactant Chemistry | Source | Type | Metal ppm | T0 | T18 | T48 | T72 | T96 | T18 – T0 | T48 – T0 | T72 – T0 | T96 – T0 |
|---|---|---|---|---|---|---|---|---|---|---|---|---|---|---|
| 167 | Pluronic L62 | EO-PO Block copolymer | BASF | Nonionic | 0 | 47 | 1088 | 1113 | 1142 | 1156 | 1041 | 1066 | 1095 | 1109 |
| 168 | | | | | 2.5 | 343 | 376 | 362 | 364 | 340 | 33 | 19 | 2 | -24 |
| 169 | | | | | 5 | 118 | 1127 | 1138 | 1175 | 1146 | 1009 | 1020 | 1057 | 1028 |
| 170 | Hampopsyl L95 | Na N-lauroyl Sarcosinate | Hampshire Chemical | Anionic | 0 | 47 | 42 | 390 | 884 | 878 | -5 | 343 | 837 | 831 |
| 171 | | | | | 2.5 | 70 | 909 | 999 | 1037 | 983 | 839 | 929 | 967 | 913 |
| 172 | | | | | 5 | 407 | 444 | 442 | 440 | 440 | 37 | 35 | 33 | 33 |
| 173 | Sodium Lauryl Sulfate | Sodium Lauryl Sulfate | VWR Scientific | Anionic | 0 | 48 | 495 | 658 | 642 | 639 | 447 | 610 | 594 | 591 |
| 174 | | | | | 2.5 | 88 | 90 | 88 | 88 | 87 | 2 | 0 | 0 | -1 |
| 175 | | | | | 5 | 231 | 244 | 233 | 238 | 232 | 13 | 2 | 7 | 1 |
| 176 | Witco | Sodium Laurylether Sulfate (2 mole EO) | Witco Chemical | Anionic | 0 | 48 | 1060 | 1021 | 957 | 923 | 1012 | 973 | 909 | 875 |
| 177 | | | | | 2.5 | 73 | 819 | 1415 | 1436 | 1447 | 746 | 1342 | 1363 | 1374 |
| 178 | | | | | 5 | 140 | 143 | 446 | 870 | 915 | 3 | 306 | 730 | 775 |
| 179 | Jeenteric CAPB LC | Cocamidopropyl betaine | Jeen International Corp | Amphoteric | 0 | 48 | 645 | 657 | 882 | 462 | 597 | 609 | 834 | 414 |
| 180 | | | | | 2.5 | 93 | 90 | 91 | 90 | 88 | -3 | -2 | -3 | -5 |
| 181 | | | | | 5 | 204 | 204 | 202 | 202 | 202 | 0 | -2 | -2 | -2 |
| 182 | Manckinate LO100 DLSS | Dilauryl sulfosuccinate | Mackintire Chemical | amphoteric | 0 | 95 | 1020 | 866 | 817 | 788 | 925 | 771 | 722 | 693 |
| 183 | | | | | 2.5 | 118 | 97 | 106 | 1165 | 1317 | -21 | -12 | 1047 | 1199 |
| 184 | | | | | 5 | 251 | 239 | 232 | 224 | 215 | -12 | -19 | -27 | -36 |
| 185 | Ammonyx LO | Lauryl Dimethyamine Oxide | Stepan Chemical | Nonionic | 0 | 44 | 28 | 35 | 45 | 28 | -16 | -9 | 1 | -16 |
| 186 | | | | | 2.5 | 972 | 390 | 118 | 115 | 105 | -582 | -854 | -857 | -867 |
| 187 | | | | | 5 | 652 | 314 | 252 | 227 | 180 | -338 | -400 | -425 | -472 |
| 188 | Hamposyl C30 | Na N-cocoyl Sarcosinate | Hampshire Chemical | Anionic | 0 | 44 | 207 | 1043 | 1041 | 1037 | 163 | 999 | 997 | 993 |
| 189 | | | | | 2.5 | 699 | 677 | 657 | 673 | 1115 | -22 | -42 | -26 | 416 |
| 190 | | | | | 5 | 510 | 554 | 576 | 589 | 593 | 44 | 66 | 79 | 83 |

TABLE 12-continued

| Example | Surfactants | Surfactant Chemistry | Source | Type | Metal ppm | T0 | T18 | T48 | T72 | T96 | T18 − T0 | T48 − T0 | T72 − T0 | T96 − T0 |
|---|---|---|---|---|---|---|---|---|---|---|---|---|---|---|
| 191 | Hamposyl M30 | Na N-myristoyl Sarcosinate | Hampshire Chemical | Anionic | 0 | 46 | 28 | 152 | 1205 | 1184 | −18 | 106 | 1159 | 1138 |
| 192 | | | | | 2.5 | 588 | 564 | 1372 | 1385 | 1389 | −24 | 784 | 797 | 801 |
| 193 | | | | | 5 | 583 | 586 | 1299 | 1382 | 1383 | 3 | 716 | 799 | 800 |
| 194 | Hampshire TL Glutamate | TEA lauroyl Glutamate | Hampshire Chemical | Anionic | 0 | 66 | 946 | 977 | 927 | 905 | 880 | 911 | 861 | 839 |
| 195 | | | | | 2.5 | 182 | 410 | 1143 | 1189 | 1178 | 228 | 961 | 1007 | 996 |
| 196 | | | | | 5 | 218 | 618 | 1104 | 1129 | 1162 | 400 | 886 | 911 | 944 |
| 197 | Tergitol 15S3 | Secondary Alcohol Ethoxylate | Dow Chemical | Nonionic | 0 | 188 | 1140 | 1178 | 969 | 880 | 952 | 990 | 781 | 692 |
| 198 | | | | | 2.5 | 180 | 340 | 1247 | 1227 | 1134 | 160 | 1067 | 1047 | 954 |
| 199 | | | | | 5 | 317 | 818 | 1350 | 1297 | 1289 | 501 | 1033 | 980 | 972 |
| 200 | Tergitol 15S7 | Secondary Alcohol Ethoxylate | Dow Chemical | Nonionic | 0 | 48 | 865 | 1077 | 766 | 577 | 817 | 1029 | 718 | 529 |
| 201 | | | | | 2.5 | 91 | 117 | 1152 | 1087 | 917 | 26 | 1061 | 996 | 826 |
| 202 | | | | | 5 | 197 | 408 | 1291 | 1224 | 1217 | 211 | 1094 | 1027 | 1020 |
| 203 | Tergitol TMN6 | Branched Secondary Alcohol Ethoxylate | Dow Chemical | Nonionic | 0 | 50 | 940 | 1128 | 784 | 614 | 890 | 1078 | 734 | 564 |
| 204 | | | | | 2.5 | 106 | 132 | 1184 | 1140 | 1048 | 26 | 1078 | 1034 | 942 |
| 205 | | | | | 5 | 215 | 480 | 1300 | 1275 | 1266 | 265 | 1085 | 1060 | 1051 |
| 206 | Tergitol TMN3 | Branched Secondary Alcohol Ethoxylate | Dow Chemical | Nonionic | 0 | 49 | 314 | 1015 | 700 | 541 | 265 | 966 | 651 | 492 |
| 207 | | | | | 2.5 | 92 | 94 | 1054 | 1014 | 876 | 2 | 962 | 922 | 784 |
| 208 | | | | | 5 | 189 | 247 | 1100 | 1128 | 1128 | 58 | 911 | 939 | 939 |
| 209 | Sulfonic TDA3B | C1-C14 Ethoxylated Alcohol | Huntsman Chemical | Nonionic | 0 | 206 | 1163 | 1183 | 948 | 809 | 957 | 977 | 742 | 603 |
| 210 | | | | | 2.5 | 260 | 372 | 1296 | 1248 | 1192 | 112 | 1036 | 988 | 932 |
| 211 | | | | | 5 | 359 | 725 | 1369 | 1366 | 1319 | 366 | 1010 | 1007 | 960 |
| 212 | Tween 20 | polyoxyethylene (20) sorbitan monolaurate | | Nonionic | 0 | 57 | 1077 | 1118 | 1087 | 730 | 1020 | 1061 | 1030 | 673 |
| 213 | | | | | 2.5 | 92 | 932 | 1116 | 867 | 719 | 840 | 1024 | 775 | 627 |
| 214 | | | | | 5 | 169 | 1080 | 1144 | 1105 | 1048 | 911 | 975 | 936 | 879 |

TABLE 12-continued

| Example | Surfactants | Surfactant Chemistry | Source | Type | Metal ppm | T0 | T18 | T48 | T72 | T96 | T18 – T0 | T48 – T0 | T72 – T0 | T96 – T0 |
|---|---|---|---|---|---|---|---|---|---|---|---|---|---|---|
| 215 | Plantaren 2000 | Alkyl polyglycoside | Cognis | Nonionic | 0 | 56 | 346 | 906 | 782 | 642 | 290 | 850 | 726 | 586 |
| 216 | | | | | 2.5 | 102 | 410 | 660 | 1104 | 1323 | 308 | 558 | 1002 | 1221 |
| 217 | | | | | 5 | 229 | 235 | 232 | 232 | 237 | 6 | 3 | 3 | 8 |
| 218 | Control | | | | 0 | 58 | 1171 | 1152 | 1168 | 1177 | 1113 | 1094 | 1110 | 1119 |
| 219 | Control (2.5 ppm) | | | | 0 | 94 | 968 | 1073 | 1180 | 1041 | 874 | 979 | 1086 | 947 |
| 220 | Control (5 ppm) | | | | 0 | 132 | 1196 | 1185 | 1228 | 1233 | 1064 | 1053 | 1096 | 1101 |
| 221 | Metals Control | | | | 2.5 | 93 | 1001 | 1080 | 1128 | 962 | 908 | 987 | 1035 | 869 |
| 222 | Metals Control | | | | 5 | 152 | 1160 | 1186 | 1228 | 1193 | 1008 | 1034 | 1076 | 1041 | seen in Table 12, the benefits of the present invention are realized with a broad array of surfactant materials. Especially preferred surfactants are those that are free or substantially free of repeat ethylene oxide units and/or have moderate to lower molecular weights. Despite the foregoing, it is noted that good results were attained with the Pluronic L62, a polyethylene oxide containing surfactant, when used in combination with the lower level of acid and metals. It is thought that the higher acid level may have affected the stability of this material, and possibly like materials.

Examples 223-236

Strobilurin Comparison

A series of experiments were conducted in order to evaluate the comparative performance of the bioactive compositions of the present invention and several commercial strobilurin based fungicides. Two bioactive formulations were used. The first, MI2, comprised a 16% aqueous citric acid solution having dissolved therein silver citrate, copper citrate and zinc citrate, each being added in an amount to provide 200 ppm of each metal, together with 0.25% sodium Lauroyl sarcosinate and 0.32% sodium lauryl sulfate, as noted above. The second, MI7, comprised a 160:1 dilution of a 16% aqueous phosphoric acid solution having dissolved therein silver citrate, copper citrate and zinc citrate, each being added in an amount to provide 200 ppm of each metal in the phosphoric acid solution. Each fungicide was evaluated at different levels. The specific formulations tested and the results attained therewith are presented in Tables 13 and 13A.

As seen in Tables 13 and 13A, the bioactive compositions of the present invention provided marked inhibition of yeast growth, even at the lower concentrations, ~5 ppm of each metal ion. On the other hand, all but two of the strobilurin based fungicide formulations tested failed to demonstrate any significant bioefficacy against yeast over the time period tested. The two formulations that provided good inhibition were at comparatively high loadings.

Examples 237-250

Strobilurin Synergy

In light of the foregoing poor performance of the strobilurins generally, a series of experiments were conducted in order to evaluate the potential synergy between the bioactive compositions of the present invention and the foregoing commercial strobilurin based fungicides. The compositions employed were the

TABLE 13

| Example | Fungicide | vol. Added | Turbidity (NTU) | | | | |
|---|---|---|---|---|---|---|---|
| | | | T0 | T1 | T18 | T26 | T50 |
| 223 | Quadris[a] | 1 | 384 | 393 | 1066 | 1139 | 1134 |
| 224 | | 2 | 767 | 772 | 1264 | 1311 | 1315 |
| 225 | | 5 | 1332 | 1332 | 1364 | 1377 | 1376 |
| 226 | Flint[b] | 1 | 418 | 424 | 1115 | 1208 | 1234 |
| 227 | | 2 | 718 | 708 | 1141 | 1299 | 1327 |
| 228 | | 5 | 1210 | 1210 | 1270 | 1265 | 1245 |
| 229 | Headline[c] | 1 | 232 | 225 | 961 | 1114 | 1137 |
| 230 | | 2 | 387 | 391 | 1066 | 1134 | 1199 |
| 231 | | 5 | 717 | 747 | 1178 | 1222 | 1241 |
| 232 | MI2 | 0.5 | 128 | 129 | 154 | 177 | 174 |
| 233 | MI2 | 1 | 414 | 384 | 366 | 366 | 352 |
| 234 | MI7 | 0.5 | 249 | 244 | 248 | 248 | 242 |
| 235 | MI7 | 1 | 311 | 302 | 283 | 283 | 277 |
| 236 | Control | | 67 | 68 | 793 | 871 | 904 |

[a]Quadris fungicide from Syngenta Crop Protections, Inc. of Greensboro, NC, USA
[b]Flint fungicide from Bayer CropScience LP of Research Triangle Park, NC, USA
[c]Headline from BASF Corporation of Research Triangle Park, NC, USA

TABLE 13A

| Example | Fungicide | vol. Added | Change in Turbidity (delta NTU) | | |
|---|---|---|---|---|---|
| | | | T18 − T1 | T26 − T1 | T50 − T1 |
| 223 | Quadris[a] | 1 | 673 | 746 | 741 |
| 224 | | 2 | 492 | 539 | 543 |
| 225 | | 5 | 32 | 45 | 44 |
| 226 | Flint[b] | 1 | 691 | 784 | 810 |
| 227 | | 2 | 433 | 591 | 619 |
| 228 | | 5 | 60 | 55 | 35 |
| 229 | Headline[c] | 1 | 736 | 889 | 912 |
| 230 | | 2 | 675 | 743 | 808 |
| 231 | | 5 | 431 | 475 | 494 |
| 232 | MI2 | 0.5 | 25 | 48 | 45 |
| 233 | MI2 | 1 | −18 | −18 | −32 |
| 234 | MI7 | 0.5 | 4 | 4 | −2 |
| 235 | MI7 | 1 | −19 | −19 | −25 |
| 236 | Control | | 725 | 803 | 836 |

[a]Quadris fungicide from Syngenta Crop Protections, Inc. of Greensboro, NC, USA
[b]Flint fungicide from Bayer CropScience LP of Research Triangle Park, NC, USA
[c]Headline from BASF Corporation of Research Triangle Park, NC, USA

TABLE 14

| Example | Bioactive | Vol. Added | Fungicide[a] | Vol. Added | Turbidity (NTU) | | | | |
|---|---|---|---|---|---|---|---|---|---|
| | | | | | T0 | T1 | T18 | T24 | T96 |
| 237 | MI2 | 0.25 | Q | 1 | 552 | 554 | 544 | 670 | 1315 |
| 238 | MI2 | 0.25 | Q | 2 | 896 | 894 | 868 | 891 | 1470 |
| 239 | MI2 | 0.5 | Q | 1 | 588 | 578 | 564 | 564 | 608 |
| 240 | MI2 | 0.25 | F | 1 | 578 | 599 | 568 | 568 | 1320 |
| 241 | MI2 | 0.25 | F | 2 | 900 | 900 | 886 | 886 | 1330 |
| 242 | MI2 | 0.25 | H | 1 | 436 | 433 | 454 | 454 | 1312 |
| 243 | MI2 | 0.25 | H | 2 | 611 | 637 | 667 | 632 | 1302 |
| 244 | MI7 | 0.25 | Q | 1 | 558 | 574 | 640 | 668 | 1273 |
| 245 | MI7 | 0.25 | F | 1 | 517 | 560 | 990 | 1197 | 1396 |
| 246 | MI7 | 0.25 | H | 1 | 465 | 476 | 605 | 587 | 1290 |
| 247 | Control | | — | | 93 | 101 | 901 | 986 | 1075 |
| 248 | MI2 | 0.5 | | | 499 | 440 | 390 | 390 | 373 |

TABLE 14-continued

|  |  |  |  |  | Turbidity (NTU) | | | | |
|---|---|---|---|---|---|---|---|---|---|
| Example | Bioactive | Vol. Added | Fungicide[a] | Vol. Added | T0 | T1 | T18 | T24 | T96 |
| 249 | MI2 | 0.25 | | | 182 | 179 | 175 | 176 | 1122 |
| 250 | MI2 | 0.5 | | | 262 | 260 | 260 | 275 | 275 |

[a]Q—Quadris fungicide from Syngenta Crop Protections, Inc. of Greensboro, NC, USA; F—Flint fungicide from Bayer CropScience LP of Research Triangle Park, NC, USA; and H—Headline from BASF Corporation of Research Triangle Park, NC, USA

TABLE 14A

|  |  |  |  |  | Change in Turbidity (delta NTU) | | |
|---|---|---|---|---|---|---|---|
| Example | Bioactive | Vol. Added | Fungicide[a] | Vol. Added | T18 − T1 | T24 − T1 | T96 − T1 |
| 237 | MI2 | 0.25 | Q | 1 | −10 | 116 | 761 |
| 238 | MI2 | 0.25 | Q | 2 | −26 | −3 | 576 |
| 239 | MI2 | 0.5 | Q | 1 | −14 | −14 | 30 |
| 240 | MI2 | 0.25 | F | 1 | −31 | −31 | 721 |
| 241 | MI2 | 0.25 | F | 2 | −14 | −14 | 430 |
| 242 | MI2 | 0.25 | H | 1 | 21 | 21 | 879 |
| 243 | MI2 | 0.25 | H | 2 | 30 | −5 | 665 |
| 244 | MI7 | 0.25 | Q | 1 | 66 | 94 | 699 |
| 245 | MI7 | 0.25 | F | 1 | 430 | 637 | 836 |
| 246 | MI7 | 0.25 | H | 1 | 129 | 111 | 814 |
| 247 | Control | | — | | 800 | 885 | 974 |
| 248 | MI2 | 0.5 | | | −50 | −50 | −67 |
| 249 | MI2 | 0.25 | | | −4 | −3 | 943 |
| 250 | MI2 | 0.5 | | | 0 | 15 | 15 |

[a]Q—Quadris fungicide from Syngenta Crop Protections, Inc. of Greensboro, NC, USA; F—Flint fungicide from Bayer CropScience LP of Research Triangle Park, NC, USA; and H—Headline from BASF Corporation of Research Triangle Park, NC, USA same as used in the previous set of examples. The specific formulations tested and the results attained therewith are presented in Tables 14 and 14A.

As seen in Tables 14 and 14A, the combination of the bioactive compositions of the present invention with the strobilurin products produced a synergy whereby even the lowest levels of the strobilurin products tested produced a significant inhibition in yeast growth, even though these products appear to increase yeast growth when used alone, as shown in the Tables 13 and 13A.

Examples 251-259

Copper/Zinc Study

A series of experiments were conducted to demonstrate the bioefficacy of binary metal systems as compared to the ternary system used in most other examples. Here a solution of MI2 was compared to a similar composition containing 300 ppm of copper and 300 ppm of zinc (i.e., a 16% aqueous citric acid solution having dissolved therein copper citrate and zinc citrate, each being added in an amount to provide 300 ppm of each metal, together with 0.25% sodium Lauroyl sarcosinate and 0.32% sodium lauryl sulfate). The two bioactive compositions were evaluated at different loadings to assess their bioefficacy. The specific formulations tested and the results attained therewith are presented in Tables 15 and 15A.

As seen in Tables 15 and 15A, both the binary (copper/zinc—Cu/Zn) and the MI2 ternary silver/copper/zinc antimicrobial bioactive compositions demonstrated comparable bioefficacy in inhibiting the growth of yeast.

TABLE 15

|  | Composition (gm) | | | | | | |
|---|---|---|---|---|---|---|---|
| Example | Cu/Zn | MI2 | T0 | T1 | T18 | T24 | T46 |
| 251 | 1 | | 776 | 586 | 468 | 463 | 436 |
| 252 | 0.5 | | 292 | 269 | 250 | 250 | 245 |
| 253 | 0.2 | | 147 | 162 | 772 | 1055 | 1075 |
| 254 | 0.1 | | 93 | 125 | 1076 | 1070 | 1036 |
| 255 | Control | | 66 | 127 | 1020 | 1012 | 1137 |
| 256 | | 1 | 830 | 633 | 547 | 522 | 500 |
| 257 | | 0.5 | 335 | 320 | 292 | 302 | 284 |
| 258 | | 0.2 | 152 | 178 | 512 | 1064 | 1098 |
| 259 | | 0.1 | 90 | 136 | 1083 | 1087 | 1067 |

TABLE 15A

|  | Composition (gm) | | | | | |
|---|---|---|---|---|---|---|
|  | Cu/Zn | MI2 | T1 − T0 | T18 − T0 | T24 − T0 | T46 − T0 |
| 251 | 1 | | −190 | −118 | −5 | −27 |
| 252 | 0.5 | | −23 | −19 | 0 | −5 |
| 253 | 0.2 | | 15 | 610 | 283 | 20 |
| 254 | 0.1 | | 32 | 951 | −6 | −34 |
| 255 | Control | | 61 | 893 | −8 | 125 |
| 256 | | 1 | −197 | −86 | −25 | −22 |
| 257 | | 0.5 | −15 | −28 | 10 | −18 |
| 258 | | 0.2 | 26 | 334 | 552 | 34 |
| 259 | | 0.1 | 46 | 947 | 4 | −20 |

Examples 260-269

Mancozeb Synergy

A further series of experiments were conducted to assess the bioefficacy, especially the synergy, of the bioactive agrichemical composition containing Mancozeb (an ethylene bisdithiocarbamate) and the MI2 bioactive acid solution (MI2). The specific formulations tested and the results attained therewith are presented in Table 16 and 16A.

As seen in Tables 16 and 16A, the mancozeb by itself was ineffective at all levels tested. The bioactive acid solution by itself provided modest bioefficacy, in spite of the very low level of antimicrobial metal ions; however, the suitable bioefficacy appeared to have been lost after 44 hours. In sharp contrast, the combination of the two, at all levels of the mancozeb, demonstrated excellent bioefficacy, even after 44 hours.

TABLE 16

| | Composition (gm) | | | | | | |
|---|---|---|---|---|---|---|---|
| Example | Mancozeb | MI2 | T0 | T2 | T18 | T24 | T44 |
| 260 | 0.5 | | 934 | 976 | 1220 | 1095 | 1091 |
| 261 | 0.4 | | 780 | 859 | 1021 | 982 | 1052 |
| 262 | 0.3 | | 624 | 717 | 1209 | 1067 | 1113 |
| 263 | 0.2 | | 392 | 489 | 1035 | 933 | 1073 |
| 264 | | 0.2 | 57 | 55 | 54 | 72 | 756 |
| 265 | 0.5 | 0.2 | 930 | 897 | 864 | 839 | 788 |
| 266 | 0.4 | 0.2 | 727 | 709 | 684 | 664 | 591 |
| 267 | 0.3 | 0.2 | 537 | 555 | 535 | 509 | 460 |
| 268 | 0.2 | 0.2 | 370 | 369 | 370 | 343 | 331 |
| 269 | Control | | 23 | 106 | 935 | 824 | 917 |

TABLE 16A

| | Composition (gm) | | | | | T44 − |
|---|---|---|---|---|---|---|
| Example | Mancozeb | MI2 | T2 − T0 | T18 − T0 | T24 − T0 | T0 |
| 260 | 0.5 | | 42 | 286 | 161 | 157 |
| 261 | 0.4 | | 79 | 241 | 202 | 272 |
| 262 | 0.3 | | 93 | 585 | 443 | 489 |
| 263 | 0.2 | | 97 | 643 | 541 | 681 |
| 264 | | 0.2 | −2 | −3 | 15 | 699 |
| 265 | 0.5 | 0.2 | −33 | −66 | −91 | −142 |
| 266 | 0.4 | 0.2 | −18 | −43 | −63 | −136 |
| 267 | 0.3 | 0.2 | 18 | −2 | −28 | −77 |
| 268 | 0.2 | 0.2 | −1 | 0 | −27 | −39 |
| 269 | Control | | 83 | 912 | 801 | 894 |

Examples 270-293

Amine Oxide Surfactant Study

A series of experiments were conducted to demonstrate the bioefficacy of amine oxide surfactants, specifically, lauryl dimethyl amine oxide (LDAO), alone and in combination with sodium lauroyl sarcosinate (NaLS) and/or sodium lauryl sulfate (SLS). In this instance a very dilute antimicrobial metal-acid solution was employed: 0.08% citric acid and 1 ppm each of silver, copper and zinc. The surfactants were employed at different levels to assess the lowest concentration at which synergy is realized. The specific formulations tested and the results attained therewith are presented in Table 17.

As seen in Table 17, even at such low concentration of acid and metal, the addition of only 0.0025% lauryl dimethyl amine oxide surfactant showed bioefficacy, with modest bioefficacy at the 0.00125% level with sodium lauroyl sarcosinate or the combination of sodium lauroyl sarcosinate and/or sodium lauryl sulfate. At 0.0025% lauryl dimethyl amine oxide, marked bioefficacy was found with addition of sodium lauroyl sarcosinate and superior bioefficacy found with addition of both sodium lauroyl sarcosinate and sodium lauryl sulfate.

Antibacterial Study

Examples 294-325

A series of experiments were conducted to evaluate the performance of the individual components of the claimed bioactive compositions as well as

TABLE 17

| Example | LDAO (w/w) % | NaLS (w/w) % | SLS (w/w) % | AG, Cu, Zn ppm | T zero | T1 | T42 | T66 | T42 − T1 | T66 − T1 |
|---|---|---|---|---|---|---|---|---|---|---|
| 270 | 0.00025 | | | | 132 | 219 | 1145 | 1133 | 926 | 914 |
| 271 | 0.00125 | | | | 141 | 211 | 1120 | 1039 | 909 | 828 |
| 272 | 0.0025 | | | | 161 | 196 | 862 | 814 | 666 | 618 |
| 273 | 0.00025 | | | 1 | 142 | 209 | 1108 | 1138 | 899 | 929 |
| 274 | 0.00125 | | | 1 | 144 | 208 | 1080 | 1076 | 872 | 868 |
| 275 | 0.0025 | | | 1 | 156 | 208 | 963 | 969 | 755 | 761 |
| 276 | | | | | 144 | 239 | 1232 | 1216 | 993 | 977 |
| 277 | 0.00025 | 0.00025 | | | 144 | 217 | 1084 | 1042 | 867 | 825 |
| 278 | 0.00125 | 0.00125 | | | 136 | 169 | 860 | 784 | 691 | 615 |
| 279 | 0.0025 | 0.0025 | | | 136 | 136 | 562 | 543 | 426 | 407 |
| 280 | 0.00025 | 0.00025 | | 1 | 150 | 216 | 1032 | 1021 | 816 | 805 |
| 281 | 0.00125 | 0.00125 | | 1 | 165 | 186 | 872 | 852 | 686 | 666 |
| 282 | 0.0025 | 0.0025 | | 1 | 174 | 184 | 181 | 295 | −3 | 111 |
| 283 | | 0.00025 | | | 149 | 248 | 1138 | 1165 | 890 | 917 |
| 284 | | 0.00125 | | | 142 | 202 | 1019 | 1018 | 817 | 816 |
| 285 | | 0.0025 | | | 147 | 207 | 1034 | 1007 | 827 | 800 |
| 286 | | | | 1 | 153 | 242 | 1167 | 1178 | 925 | 936 |
| 287 | | | | | 165 | 270 | 1223 | 1207 | 953 | 937 |
| 288 | 0.00025 | 0.00025 | 0.00025 | | 178 | 272 | 1094 | 1006 | 822 | 734 |
| 289 | 0.00125 | 0.00125 | 0.00125 | | 167 | 242 | 800 | 686 | 558 | 444 |
| 290 | 0.0025 | 0.0025 | 0.0025 | | 224 | 212 | 605 | 550 | 393 | 338 |
| 291 | 0.00025 | 0.00025 | 0.00025 | 1 | 171 | 252 | 1039 | 1010 | 787 | 758 |

TABLE 17-continued

| Example | LDAO (w/w) % | NaLS (w/w) % | SLS (w/w) % | AG, Cu, Zn ppm | T zero | T1 | T42 | T66 | T42 – T1 | T66 – T1 |
|---|---|---|---|---|---|---|---|---|---|---|
| 292 | 0.00125 | 0.00125 | 0.00125 | 1 | 260 | 258 | 862 | 872 | 604 | 614 |
| 293 | 0.0025 | 0.0025 | 0.0025 | 1 | 264 | 257 | 242 | 242 | −15 | −15 | various combinations thereof, including, the claimed compositions themselves, in suppressing the growth of various bacteria. *Escherichia coli* (*E. coli*), *Pseudomonas aeruginosa* (*P. aeruginosa*) and *Staphylococcus aureus* (*S. aureus*) were selected as a test organisms as they are generally accepted in the industry as indicator organisms for a wide variety of bacteria. Two different test methodologies were evaluated, one testing the efficacy in a growth broth media and the other testing inhibition in plated growth media.

Examples 294-305

In the first set of experiments a growth medium was prepared by adding 10 grams of nutrient medium (Difco Sabouraud dextrose broth from BD of Franklin Lakes, N.J., USA) to 300 ml of distilled water. The 20 ml aliquots of the growth medium were dispensed into sterile into 40 ml borosilicate glass vials with Teflon lined caps (VWR International Cat. No. 15900-004). The vials were inoculated with the bacteria using a sterile loop and the vials then incubated at 37° C. A bioactive composition according to the invention was then added to certain vials, the bioactive composition was (MI2), as described above, comprising a 16% aqueous citric acid solution having dissolved therein silver citrate, copper citrate and zinc citrate, each added in an amount to provide 200 ppm of each metal, together with 0.25% sodium Lauroyl sarcosinate and 0.32% sodium lauryl sulfate. The turbidity of each mixture was then determined and the vial transferred to an incubator at 30° C. Turbidity measurements were performed as in the above cited yeast studies. Each vial was periodically removed from the incubator and the mixture in the vials assessed for turbidity. The specific formulations tested, the timing for each turbidity evaluation, and the results attained thereby were as set forth in Table 18.

As with the yeast study, the concentration of the metals refers the approximate amount of each metal, copper, silver and zinc. The concentrations do not account for the volume of MI2 added; thus, the concentrations presented are on the basis of a 20 ml total volume.

As seen in Table 18, there was short term increase in turbidity. Since it was not anticipated that any significant growth would have manifested in such a short period of time, it is believed that the initial increase in turbidity resulted from a denaturation of proteins in the broth and/or bacterial proteins. Regardless, the longer term results show excellent bacterial inhibition with the compositions according to the present invention.

TABLE 18

| Example | Bacterium | MI2 (ml) | Metals ppm | Time (hours) | | | | |
|---|---|---|---|---|---|---|---|---|
| | | | | T0 | T0.5 | T18 | T24 | T96 |
| 294 | *E. coli* | 0 | 0 | 15.3 | 16 | 119 | 136 | 264 |
| 295 | | 0.5 | 5 | 131 | 135.3 | 165 | 162 | 162 |
| 296 | | 1 | 10 | 445 | 454 | 481 | 480 | 480 |
| 297 | | 2 | 20 | 1039 | 1080 | 1135 | 1140 | 1009 |
| 298 | *p. aeruginosa* | 0 | 0 | 35.8 | 37.8 | 158 | 383 | 436 |
| 299 | | 0.5 | 5 | 197 | 207 | 250 | 262 | 261 |
| 300 | | 1 | 10 | 705 | 735 | 782 | 808 | 807 |
| 301 | | 2 | 20 | 1011 | 1057 | 1121 | 1159 | 1146 |
| 302 | *S. aureus* | 0 | 0 | 46 | 45 | 148 | 184 | 406 |
| 303 | | 0.5 | 5 | 215 | 163 | 173 | 183 | 184 |
| 304 | | 1 | 10 | 643 | 494 | 326 | 309 | 276 |
| 305 | | 2 | 20 | 1203 | 1032 | 595 | 525 | 281 |

Example 306

In this experiment, six 25 mm sterile coverslips were placed into separate 100×15 mm sterile Petri dishes and two of each inoculated with 100 µl of one of three TSB broths: each broth containing one of *E. coli*, *P. aeruginosa* and *S. aureus* that had been allowed to incubate for 48-54 hours. In order to afix the inoculum to the coverslips, the Petri dishes were placed on a low temperature hot plate for approximately 5 minutes. One of each of the inoculated Petri dishes was set aside as positive controls. The other was sprayed with 4 sprays of a 4:1 dilution of the bioactive compositions MI2. After 2-3 minutes the coverslips and liquid contents of each Petri dish was aseptically transferred into separate vials containing 20 ml of TSB and incubated at 37° C. for 24 hours. Negative controls were prepared by placing non-inoculated sterile coverslips into the 20 ml TSB and incubating as well. After 24 hours, no growth was observed with the negative controls or with those inoculated coverslips that had been sprayed with the bioactive composition of the present invention. Visual growth was observed in two of the positive controls (i.e., those vials containing the inoculated coverslips that had not been sprayed): the positive control for *p. aeruginosa* failed to show visual growth. It is believed that the failure of the later to show growth resulted from overheating the inoculum during the fixturing step.

Example 307

In this experiment, two Trypticase soy agar (TSA) plates were inoculated with 500 µl of one of three TSB broths for a total of 6 inoculated plates: each broth contained one of *E. coli*, *P. aeruginosa* and *S. aureus* that had been allowed to incubate for 48-54 hours. The inoculum was evenly spread across the surface of the plate with a sterile loop. A 15 mm diameter disc of filter paper that had been dipped in a 4:1 dilution of the MI2 bioactive composition was placed in the center of one of each set of inoculated plates and all plates were placed in an incubator at 37° C. for 24 hours. Non-inoculated control plates were also placed in the incubator as well.

was then added to each of the ten tubes for that series and the tubes incubated for 24 hours at 26° C. Because the acid solution caused considerable cloudiness of the tubes to which it was added, macroscopic evaluation was not possible. Instead, each tube was subcultured onto corresponding agar plates. The observed growth was as indicated in Table 19 (a "+" indicates visual growth and a "−" no growth).

TABLE 19

|  | Test Tube | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| Metals concentration* (ppm) | 200 | 50 | 25 | 12.5 | 6.75 | 3.125 | 1.56 | 0.782 | 0.391 | 0.195 |
| C. michiganese | − | − | − | − | − | − | + | + | + | + |
| P. syringae | − | − | − | − | − | + | + | + | + | + |
| E. amylovora | − | − | − | − | − | − | + | + | + | + |

*concentration of each metal, the total metal content is 3 time the number presented.

After 24 hours, visual growth was observed. No bacterial growth was seen in the non-inoculated plates. Growth was observed on all of the inoculated plates; however, in those plates wherein the treated filter paper had been placed, no growth was seen on or near the filter paper. Each treated filter paper disc manifested a clear zone of inhibition of bacterial growth.

Based on the results presented in Table 19, the MIC of MI2 is 3.125 ppm for *C. michiganese* and for *E. amylovora* and 6.75 ppm for *P. syringae*. The bioefficacy of such low levels are anticipated to show synergy when combined with conventional fungicides/bactericides for these target organisms.

Example 308

In this experiment, two Trypticase soy agar (TSA) plates were innoculated with 500 μl of one of three TSB broths for a total of 6 inoculated plates: each broth contained one of *E. coli*, *P. aeruginosa* and *S. aureus* that had been allowed to incubate for 48-54 hours. The inoculum was evenly spread across the surface of the plate with a sterile loop. One of each inoculated plates was then sprayed, approximately 24 times, with the 4:1 dilution of the MI2 bioactive composition. The inoculated plates plus a set of plates non-inoculated control plates were placed in an incubator at 37° C. for 24 hours.

After 24 hours, visual growth was observed on inoculated, but untreated plates whereas no bacterial growth was seen in the non-inoculated plates or in those inoculated plates that had been sprayed with the diluted bioactive composition.

Examples 309

Bacterial MIC Study

A study was conducted to determine the minimum inhibitory concentration (MIC) of the MI2 acid solution, i.e., 200 ppm of each of silver, copper and zinc metal (see Examples 72-79). Three different bacteria were evaluated, *Clavibacter michiganese*, *Pseudomonas syringae* and *Erwinia amylovora*, each in a different growth medium appropriate for that bacteria, namely brain infusion agar/broth, nutrient agar/broth, and nutrient glucose agar/broth, respectively. In conducting the test, three sets of 10 test tubes were prepared, one set for each bacteria, and labeled 1 to 10. 0.5 ml of the appropriate broth was placed in each of test tubes 2 through 10. Then 0.5 ml of the MI2 solution was added to each of test tubes 1 and 2. 0.5 ml of the contents of test tube 2 was then transferred to test tube 3 and then 0.5 ml of test tube 3 to test tube 4 and so on to test tube 9. 0.5 ml or test tube 9 was discarded. A 0.5 ml suspension of each bacteria to be tested Example 326

Post Harvest Protectant

To assess the viability of the bioactive compositions of the present invention as a pre-harvest/post-harvest foodstuff protective composition, a bioactive composition according to the present invention was prepared comprising 5 ppm silver, 5 ppm copper, and 5 ppm zinc (all as ion species), 0.05% sodium lauroyl sarcosinate and 0.05% sodium lauryl sulfate in 0.4% citric acid. The composition was applied by spraying to a ripe peach. A second ripe peach was treated with a mancozeb solution and a third ripe peach was left untreated. All three peaches were allowed to sit in a humid environment for several weeks. Following several weeks, the untreated peach was found to have brown rot covering most of its surface. The mancozeb treated peach manifested both brown rot and mold growth on most of its surface. On the other hand, the peach treated with the bioactive composition of the present invention shown no outward signs of rot or decay. Its color was still vibrant and its texture soft, but firm. Such results demonstrate the huge potential of these bioactive materials as pre-harvest and post-harvest treatments for foodstuffs for protection against pathogenic, indicator and/or spoilage bacteria.

Example 327

*Alternaria* Leaf Spot

To demonstrate the efficacy of the bioactive compositions on live plants, a comparative study was conducted comparing the efficacy of a bioactive composition according to the present invention to two commercial products, Eagle 40WP, a myclobutanil based (40 wt %) fungicide available from Dow AgroSciences LLC of Indianapolis, Ind., USA, and Scala SC, a pyrimethanil based (54.6 wt %) fungicide available from Bayer CropScience LP of Research Triangle Park, NC, USA. Additional evaluations were conducted to assess the potential for synergy between the inventive bioactive compositions and Eagle 40WP. The bioactive composition according to the present invention comprised a 16% aqueous citric acid solution having dissolved therein silver citrate, copper citrate, and zinc citrate in an amount to provide 200 ppm of each metal in the solution, 0.25% sodium lauroyl sarcosinate and 0.32% sodium lauryl sulfate (MI6). This solution was diluted at rates of 40:1 and 20:1 for application to the plants thereby providing a solution containing ~5 ppm and ~10 ppm of each metal as sprayed.

*Pittosporum tobira* "Wheeleri" rooted cuttings were planted in standard 4 inch pots containing Sunshine Mix No. 1 and fertilized with ½ tsp. Osmocote Plus 15-9-12. The plants were placed in a heated greenhouse with poly and shade cloth covering the top and sides and flood irrigated as needed. After 44 days, the plants were treated with the various antifungal treatments—12 plants were treated with each treatment. Thereafter, the plants were placed in individual clear plastic bags (high humidity) in the greenhouse for the duration of the study. The plants were irrigated from below using an ebb and flood bench to assure no water application to their leaves during the trial. The plants were subsequently inoculated by spraying with a spore suspension of a culture of *Alternaria pittospori* mixed with sterilized water 4 days following the initial treatment. The treatments were reapplied 7 days and 17 days following inoculation. All treatments were applied by spray until the surfaces of the plant leaves were fully wetted (began to drip). Two sets of plants were used as positive and negative controls: the first set was treated with water only (Treatment A) and not inoculated. The second set was also treated with water only, but was also inoculated concurrent with the others. The specific formulations for each of the treatments were as set forth in Table 20.

TABLE 20

| Treatment | Composition | Dilution |
| --- | --- | --- |
| A | Water - non-inoculated | |
| B | Water - inoculated | |
| C | MI6 | 6.25 ml/250 ml water |
| D | MI6 | 12.5 ml/250 ml water |
| E | MI6/Eagle 40 WP | 6.25 ml/250ml water// 1.5 oz/100 gal water |
| F | MI6/Eagle 40 WP | 6.25/250 ml water// 3.0 oz/100 gal water |
| G | MI6/Eagle 40 WP | 12.5 ml/250 ml water// 1.5 oz/100 gal water |
| H | Eagle 40 WP | 1.5* oz /100 gal water |
| I | Eagle 40 WP | 3.0 oz/100 gal water |
| J | Scala | 9.0* oz*/100 gal water |

*manufacturer recommended application rates

Six days following the second treatment, the plants were evaluated for *Alternaria* leaf spot by visual inspection. The results of the leaf spot evaluation were as presented in Table 21. As seen in Table 21, those plants treated with the lowest concentration of the bioactive composition (with ~5 ppm of each metal ion—Treatment C) still showed nearly a 50% drop in leaf spot formation. Doubling the bioactive composition (~10 ppm of each metal ion—Treatment D) reduced leaf spot by over 75%. Somewhat similar results were found with the two dilutions of the commercial fungicide Eagle 40WP with the lower concentration (Treatment H) reducing leaf spot by about 30% while the higher concentration (Treatment I) reduced leaf spot by 80%. Combining the two provided marked improvement with, oddly enough, the combination of the two lowest concentrations providing nearly complete inhibition of leaf spot manifestation. The other commercial fungicide Scala SC provided no inhibition and, appeared to promote the manifestation of leaf spot.

TABLE 21

| | Plant No. | | | | | | | | | | | | |
| --- | --- | --- | --- | --- | --- | --- | --- | --- | --- | --- | --- | --- | --- |
| Treatment | 1 | 2 | 3 | 4 | 5 | 6 | 7 | 8 | 9 | 10 | 11 | 12 | Mean |
| A. | 0 | 0 | 0 | 0 | 0 | 0 | 0 | 0 | 0 | 0 | 0 | 0 | 0.0 |
| B. | 4 | 5 | 0 | 15 | 35 | 20 | 40 | 15 | 10 | 25 | 30 | 20 | 18.2 |
| C. | 0 | 0 | 0 | 0 | 0 | 5 | 35 | 35 | 40 | 0 | 0 | 0 | 9.6 |
| D. | 0 | 1 | 0 | 0 | 5 | 0 | 0 | 0 | 0 | 5 | 10 | 30 | 4.2 |
| E. | 0 | 0 | 0 | 0 | 0 | 1 | 0 | 0 | 5 | 0 | 0 | 0 | 0.5 |
| F. | 0 | 0 | 0 | 0 | 0 | 0 | 25 | 0 | 0 | 5 | 10 | 0 | 3.3 |
| G. | 0 | 0 | 0 | 0 | 0 | 0 | 0 | 15 | 10 | 0 | 0 | 0 | 2.1 |
| H. | 0 | 0 | 0 | 5 | 10 | 0 | 30 | 35 | 40 | 10 | 10 | 15 | 12.9 |
| I. | 2 | 0 | 0 | 0 | 1 | 0 | 10 | 25 | 5 | 0 | 0 | 0 | 3.5 |
| J. | 25 | 25 | 10 | 5 | 15 | 25 | 30 | 0 | 40 | 40 | 40 | 20 | 22.9 |

Eleven days following the last treatment, disease severity was once again assessed. However, owing to the number of spots which made giving a numerical assessment impossible, disease severity was recorded using the following scale: 1—1—no disease, 2—slight, 3—moderate, 4—severe to 5—plant dead. The results are presented in Table 22.

TABLE 22

| | Plant No. | | | | | | | | | | | | |
| --- | --- | --- | --- | --- | --- | --- | --- | --- | --- | --- | --- | --- | --- |
| Treatment | 1 | 2 | 3 | 4 | 5 | 6 | 7 | 8 | 9 | 10 | 11 | 12 | Mean |
| A. | 2 | 1 | 1 | 1 | 1 | 1 | 1 | 1 | 1 | 1 | 1 | 1 | 1.1a |
| B. | 2.5 | 2.5 | 1 | 4 | 3.5 | 3 | 4 | 2 | 2 | 3 | 3 | 3.5 | 2.8c |
| C. | 1 | 1 | 1 | 1 | 1 | 2 | 2 | 2.5 | 2.5 | 2 | 2 | 1 | 1.6a |
| D. | 1 | 1 | 2 | 1 | 2 | 1 | 1 | 1 | 1 | 1 | 2 | 2.5 | 1.4a |
| E. | 1 | 1 | 1 | 1 | 1 | 1 | 2 | 1 | 1 | 1 | 1 | 2 | 1.2a |
| F. | 1 | 2 | 2 | 1 | 1 | 1 | 2 | 1 | 1 | 1 | 2 | 1 | 1.3a |
| G. | 1 | 1 | 1 | 1 | 1 | 1 | 2 | 2 | 2 | 1 | 1 | 1 | 1.2a |
| H. | 2 | 2 | 1 | 2.5 | 2 | 2 | 2.5 | 3 | 3 | 2 | 2.5 | 2.5 | 2.2b |
| I. | 2.5 | 1 | 1 | 1 | 2 | 2 | 2 | 2 | 1 | 2 | 2 | 2 | 1.7a |
| J. | 3.5 | 4 | 3 | 3 | 3 | 4 | 3.5 | 2.5 | 4 | 4 | 4 | 4 | 3.5d |

As shown in Table 22, the bioactive compositions according to the present invention provided excellent protection against leaf spot, with those plants treated at the higher level and in combination with the commercial fungicide Eagle 40WP showing nearly the same level of disease as those that had not been inoculated at all. On the contrary, the Eagle alone, even at the recommended application rate, proved less efficacious than the bioactive composition. Finally, the Scala once again failed to show any efficacy and, in fact, proved more detrimental. It was suspected that the Scala treated plants manifested both leaf spot disease and phytotoxicity. None of the plants treated with the bioactive composition or the commercial Eagle fungicide showed evidence of phytotoxicity.

Although the present invention has been described with respect to the foregoing specific embodiments and examples, it should be appreciated that other embodiments utilizing the concept of the present invention are possible without departing from the scope of the invention. The present invention is defined by the claimed elements and any and all modifications, variations, or equivalents that fall within the spirit and scope of the underlying principles.

I claim:

1. A method of preserving and/or delaying the onset of spoilage in freshly harvested fruits, vegetables, nuts and grains said method comprising wetting or coating the surface of the freshly harvested fruits, vegetables, nuts and grains with a protective solution comprising either:
  (A) I) a bioactive composition effective in killing and/or controlling or inhibiting the growth and proliferation of microorganisms responsible for the decay and spoilage of foods and foodstuffs at the level applied, II) water or an aqueous-based diluent, and III) 0.5 to 10 weight percent based on the weight of the protective solution of a binder or other adhesive-type component for ensuring long term adherence of the bioactive composition to the surface of the freshly harvested fruits, vegetables, nuts and grains selected from the group consisting of a wax, a soluble film-forming natural or synthetic resin, a film-forming poivmerizable resin, a film forming polymer, gum arabic, a latex, a natural phospholipid and a consumable binder material;

wherein the bioactive composition comprises a) a carboxylic acid selected from the group consisting of citric acid, valeric acid, itaconic acid, acetic, citriconic acid, lactic acid, malic acid, succinic acid, aldaric acid, proprionic acid, malonic acid, maleic acid, salicylic acid, glutaric acid, tartaric acid, and benzoic acid, b) at least one source of antimicrobial metal ions which source or sources are collectively capable of releasing metal ions selected from the group consisting of a combination of silver and copper ions, a combination of silver and zinc ions, a combination of copper and zinc ions and a combination of silver, copper and zinc ions, and c) at least one anionic, non-ionic and/or amphoteric surfactant; or (B) (A) I) a bioactive composition effective in killing and/or controlling or inhibiting the growth and proliferation of microorganisms responsible for the decay and spoilage of foods and foodstuffs at the level applied, II) water or an aqueous-based diluent, and III) optionally, 0.5 to 10 weight percent based on the weight of the protective solution of a binder or other adhesive-type component for ensuring long term adherence of the bioactive composition to the surface of the freshly harvested fruits, vegetables, nuts and grains;

wherein the bioactive composition comprises a) a carboxylic acid selected from the group consisting of citric acid, valeric acid, itaconic acid, acetic, citriconic acid, lactic acid, malic acid, succinic acid, aldaric acid, proprionic acid, malonic acid, maleic acid, salicylic acid, glutaric acid, tartaric acid, and benzoic acid, b) at least one source of antimicrobial metal ions which one or more sources are collectively capable or releasing a combination of silver, copper and zinc ions, and c) at least one anionic, non-ionic and/or amphoteric surfactant;

wherein in both (A) and (B), i) the acid is present in at least a two times molar excess relative to the antimicrobial metal ions, ii) the pH of the acid/metal ion combination in purified water is from 1.5 to less than 6; iii) the concentration of the carboxylic acid is from about 0.01 to about 10 weight percent based on the weight of the protective solution, iv) the concentration of the antimicrobial metal ions in the protective solution is from about 2 ppm to about 1000 ppm, and v) the concentration of the surfactant is from about 0.001 to about 3 weight percent based on the weight of the protective solution.

2. The method of claim 1 wherein the carboxylic acid is present in an amount of from 0.1 to 4 weight percent of the protective solution.

3. The method of claim 1 wherein the protective solution is solution (B).

4. The method of claim 1 wherein the pH is from about 2 to about 5.

5. The method of claim 1 wherein the molar excess of acid relative to antimicrobial metal ions is at least 5 times molar excess.

6. The method of claim 1 wherein the antimicrobial metal ions are present at a level of from about 2 ppm to about 500 ppm.

7. The method of claim 1 wherein the antimicrobial metal ions are present at a level of from about 5 ppm to about 150 ppm.

8. The method of claim 1 wherein the total amount of antimicrobial metal ions is no more than 50 ppm.

9. The method of claim 1 wherein the concentration of the acid is from about 0.1 to about 4 weight percent based on the weight of the protective solution.

10. The method of claim 1 wherein the surfactant is sodium lauroyl sarcosinate, sodium lauryl sulfate, lauryl dimethyl amine oxide, a combination of sodium lauroyl sarcosinate and sodium lauryl sulfate, a combination of sodium lauryl sulfate and lauryl dimethyl amine oxide, a combination of sodium lauroyl sarcosinate and lauryl dimethyl amine oxide, or a combination of sodium lauroyl sarcosinate, sodium lauryl sulfate and lauryl dimethyl amine oxide.

11. The method of claim 1 wherein the protective solution is solution (B) and the binder material is present and is selected from a wax, a soluble film-forming natural or synthetic resin, a film-forming polymerizable resin, a film forming polymer, gum arabic, a latex, or a natural phospholipid.

12. The method of claim 1 wherein the protective composition is applied to the freshly harvested fruits, vegetables, nuts and grains after processing but before packaging.

13. The method of claim 1 wherein the freshly harvested fruits, vegetables, nuts and grains are dipped in the protective bioactive solution.

14. The method of claim 1 wherein the freshly harvested fruits, vegetables, nuts and grains are sprayed or coated with the protective bioactive solution.

15. The method of claim 1 wherein the surfactant is selected from the group consisting of sulfonates, sulfates, sulfosuccinates, sarcosinates, mono- and di-glycerides, amine oxides, ether carboxylates, betaines, suflobetaines, and glycinates.

16. The method of claim 1 wherein a combination of two or more surfactants is employed, each surfactant independently selected from the group consisting of sulfonates, sulfates, sulfosuccinates, sarcosinates, mono- and di-glycerides, amine oxides, ether carboxylates, betaines, suflobetaines, and glycinates.

17. The method of claim 1 wherein the at least one surfactant is selected from the group consisting of sulfonates, sulfates, sulfosuccinates, sarcosinates, and amine oxides and combinations of any two or more thereof.

18. The method of claim 1 wherein the carboxylic acid is selected from citric acid, salicylic acid, glutaric acid, and tartaric acids.

19. The method of claim 1 wherein the binder is present and is a film forming polymer.

20. The method of claim 1 wherein the binder is present and is a consumable binder material.

21. The method of claim 1 wherein the protective solution further comprises one or more conventional additives, agents or actives for food and foodstuff protection and/or preservation.

22. The method of claim 21 wherein the one or more conventional additives, agents or actives include fillers, diluents, dyes, adjuvants, emulsifiers, dispersing agents, wetting agents, thickeners, thixotropic agents, and defoaming agents.

* * * * *